United States Patent [19]

Robins et al.

[11] Patent Number: 5,041,426

[45] Date of Patent: * Aug. 20, 1991

[54] IMMUNE SYSTEM ENHANCING 3-β-D-RIBOFURANOSYLTHIAZOLO[4,5-D]PYRIMIDINE NUCLEOSIDES AND NUCLEOTIDES

[75] Inventors: Roland K. Robins, Irvine; Howard B. Cottam, Fallbrook, both of Calif.

[73] Assignee: Brigham Young University, Provo, Utah

[*] Notice: The portion of the term of this patent subsequent to Nov. 14, 2006 has been disclaimed.

[21] Appl. No.: 236,366

[22] Filed: Aug. 25, 1988

Related U.S. Application Data

[63] Continuation-in-part of Ser. No. 136,020, Dec. 21, 1987, Pat. No. 4,880,784.

[51] Int. Cl.$^5$ ............................................. A61K 31/70
[52] U.S. Cl. ...................................... 514/43; 514/48; 536/24; 536/28
[58] Field of Search ............................ 514/43, 45–48; 536/24, 26–29

[56] References Cited

U.S. PATENT DOCUMENTS 4,746,651 5/1988 Goodman ............................ 514/45

Primary Examiner—Johnnie R. Brown
Assistant Examiner—L. Eric Crane
Attorney, Agent, or Firm—Herb Boswell

[57] ABSTRACT

Compounds of the structure:

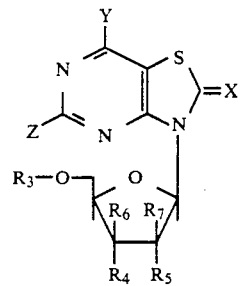

wherein $R_4$, $R_5$, $R_6$ and $R_7$ individually are H, OH or $C_1$-$C_{18}$ O-acyl and $R_3$ is H, $C_1$-$C_{18}$ acyl or

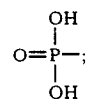

or $R_5$ and $R_7$ are H or OH, $R_6$ is H and together $R_3$ and $R_4$ are

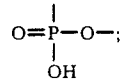

and X is =O or =S; Y is —OH, —SH, —Nh$_2$ or halogen; and Z is H, —Nh$_2$, —OH or halogen; wherein halogen is Cl or Br; or pharmaceutically acceptable salt thereof are useful as antivirals, antitumors, antimetastatics and as immune system enhancers.

23 Claims, No Drawings

IMMUNE SYSTEM ENHANCING 3-β-D-RIBOFURANOSYLTHIAZOLO[4,5-D]PYRIDIMINE NUCLEOSIDES AND NUCLEOTIDES

CROSS REFERENCE TO RELATED APPLICATIONS

This application is a continuation in part of prior application Ser. No. 136,020, filed Dec. 21, 1987 entitled Antiviral Antitumor Immune System Enhancing Nucleosides and Nucleotides in the Name of Roland K. Robins and Howard B. Cottam, that issued on Nov. 14, 1989, as U.S. Pat. No. 4,880,784.

TECHNICAL FIELD

This invention is directed to new and improved antiviral, antitumor and immune system enhancing nucleosides and nucleotides.

BACKGROUND OF INVENTION

The immune system is an inherently complex system that serves its host by providing natural resistance and recovery against both pathogens of an external source as well as aberrant 'self' cells, i.e. tumor growth. It provides both 'natural', i.e. inborn and unchanging, or 'acquired', i.e. adaptive immune response.

For the most part the immune system is innocuous to 'self.' The immune system is able, in most instances, to recognize 'self,' its host, and differentiate between 'self' and non-self. That is the immune system is 'self tolerant.' In certain instances, however, the immune system does attack its host as if it were foreign resulting in autoimmunity or autoimmune disease or hypersensitivity expressed in the form of allergies, certain forms of kidney disease and the like.

While for the most part an effective and active immune system confers biological advantages for the host, modern medicine has sought in certain instances to repress the immune system because of autoimmunity hypersensitivity in graft or organ transplant and in other instances stimulate the immune system by immunization. It is therefore advantageous in certain instances to attempt to stimulate the immune system against pathogen or tumor attack and in other instances to repress the immune system when it becomes self destructive to the host or for organ transplant or the like.

While most molecular entities either synthetic or natural which are known to stimulate the immune system are large molecules such as interferon, poly I:C or large messenger proteins, certain small molecules have also been shown to modulate the immune system as well. Of the small molecular entities the nucleoside 3-deaza-adenosine has been indicated in U.S. Pat. No. 4,309,419 to Walberg, et al., which issued Jan. 5, 1982, as being an inhibitor of the immune response. Other nucleosides, most notably 8-bromoguanosine, 8-mercaptoguanosine and 7-methyl-8-oxoguanosine have been noted as showing stimulation of the immune system.

Certain components of the immune system are cellular in nature while others are humoral, that is they exist free in serum or other body fluids. Adaptive immunity is based upon special properties of lymphocytes. The lymphocyte populations are generally divided between T lymphocytes commonly called T cells and B lymphocytes commonly called B cells. The T lymphocytes undergo a maturation processing in the thymus whereas the B lymphocytes are continuously generated in the bone marrow and are responsible for the production of antibodies. The lymphocytes freely circulate in the blood and from blood gain access to the tissues from which they are collected and recycled back via the lymph systems including the lymph glands and spleen.

Components of the cellular immune mechanisms include macrophages (hereinafter also referred to as MAC's), polymorphonuclear leukocytes commonly called PMN, mast cells and other cellular or molecular entities such as interferon and the like. Further, complements which are a series of proteins present in the serum can be activated by other immune components or directly by pathogens such as bacteria or the like.

Natural killer cells, hereinafter also identified as NK cells, constitute a group of cells which are concerned with natural immunity. These are lymphoid cells which are generally found in at least the young of all mammalian species and can be readily elicited in older animals. They generally exert a selective cytotoxicity against a range of target cells mostly malignant tumor cells.

The B cells produce antibody. Antibodies are a group of proteins of various classes including IgG, IgM, IgA, IgD, IgE. Not all specific antibody classes are present in different animal species. Generally the higher up on the evolutionary chain of animals the more antibody species present with warm blooded mammals generally having a full contingent of the different antibody species. The immune system is capable of modifying certain regions on the antibody proteins allowing the antibody protein to bind with specific antigens of various origins. These include pathogens, parts of pathogens such as cellular wall polysaccharide molecules, large protein or the like, as well as other foreign debris such as pollen and even in autoimmune diseases portions of the host itself. Some antibody production by the B cells is independent of the T cells while other antibody production is T cell dependent.

There are several groups of T cells including helper T cells which stimulate other T cells and B cells for the production of antibody, suppressor T cells which modulate the immune response to keep it from overwhelming the host, cytotoxic T cells (CTL's) which are very important against pathogens especially viral pathogens and delayed hypersensitive T cells which are important in attracting and activating a variety of other cells, including the macrophages.

The immune system is important in protecting the host against a variety of pathogens including bacteria, viruses, protozoa, parasitic worms such as flukes, tapeworms and round worms, fungi, and tumor cells of the host which become parasitic on the host. The antiviral activity of the immune system is generally associated with the T cells whereas the natural antitumor ability of the host resides with the macrophages, the natural killer cells, certain non-T and non-B myeloid cells and with certain portions of the complement system.

As is evident, the immune system is a very complex system which is extremely important to the host for protection of the host against outside pathogens as well as against internal aberrant cells. Catastrophic effects to the host can result when pathogens, tumors or the like overwhelm the immune system of the host. It has even been suggested that tumors may have the ability to depress or subvert the hosts immune system. This is supported by the recognition of clinicians that viral and bacteria infections can be a major contributor to the deaths among tumor patients.

In view of the above it is evident that there is a need for new and improved antiviral and antitumor immune enhancing agents.

BRIEF DESCRIPTION OF THE INVENTION

The present invention relates to a novel class of nucleosides and nucleotides of the thiazolo[4,5-d] pyrimidine ring system.

In accordance with the invention, disclosed are compounds of the formula:

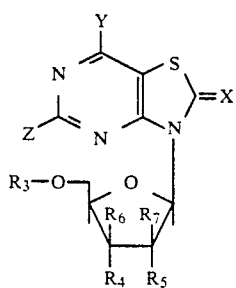

wherein $R_4$, $R_5$, $R_6$ and $R_7$ individually are H, OH or $C_1$-$C_{18}$ O-acyl and $R_3$ is H, $C_1$-$C_{18}$ acyl or

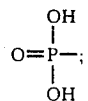

or $R_5$ and $R_7$ are H or OH, $R_6$ is H and together $R_3$ and $R_4$ are

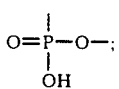

and X is =O or =S; Y is —OH, —SH, —NH$_2$ or halogen; and Z is H, —NH$_2$, —OH or halogen; wherein halogen is Cl or Br; or a pharmaceutically acceptable salt thereof.

A presently preferred group of compounds of the invention are compounds of the formula:

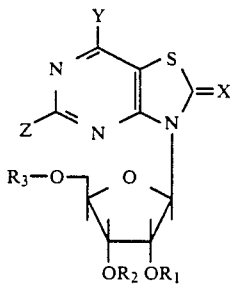

wherein $R_1$ and $R_2$ individually are H or $C_1$-$C_{18}$ acyl and $R_3$ is H, $C_1$-$C_{18}$ acyl or

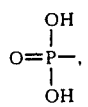

or $R_1$ is H and together $R_2$ and $R_3$ are

and X is =O or =S; Y is —OH, —SH, —NH$_2$ or halogen; and Z is H, —NH$_2$, —OH or halogen; wherein halogen is Cl or Br; or a pharmaceutically acceptable salt thereof.

Particularly preferred are compounds wherein Z is —NH$_2$, Y is —OH, X is =O or =S and $R_1$, $R_2$ and $R_3$ each are H.

The compounds of the invention are useful as immune system enhancers and have certain immune system properties including modulation, mitogenicity, augmentation and/or potentiation or they are intermediates for compounds which have these properties. The compounds have been shown to express effects on at least the natural killer, macrophages and lymphocyte cells of the immune system of a host. Because of these properties they are useful as antiviral, antitumor and antimetastatic agents or as intermediates for antiviral, antitumor and antimetastatic agents. They can be used to treat an affected host by serving as the active ingredients of suitable pharmaceutical compositions.

In accordance with the invention, compounds of the invention are utilized to treat viral diseases in host mammals by administering to the mammal a therapeutically effective amount of the compounds.

Further in accordance with the invention, compounds of the invention are utilized to treat tumors in host mammals by administering to the mammal a therapeutically effective amount of the compounds.

Also in accordance with the invention, compounds of the invention are utilized to inhibit tumor metastasis in host mammals by administering to the mammal a therapeutically effective amount of the compounds.

Additionally in accordance with the invention, compounds of the invention are utilized to stimulate the immune system of a mammalian host by administering to the mammalian host a therapeutically effective amount of the compounds.

Additionally in accordance with the invention, 5-amino-3-$\beta$-D-ribofuranosylthiazolo[4,5-d]pyrimidine-2,7(6H)-dione is utilized to enhance natural killer immune cells in a host by administering to the host a therapeutically effective amount of 5-amino-3-$\beta$-D-ribofuranosylthiazolo[4,5-d]pyrimidine-2,7(6H)-dione as the active component in a pharmaceutical composition.

Additionally in accordance with the invention, 5-amino-3-$\beta$-D-ribofuranosylthiazolo[4,5-d]pyrimidine-2,7(6H)-dione is utilized to enhance macrophage cells in a host by administering to the host a therapeutically effective amount of 5-amino-3-$\beta$-D-ribofuranosylthiazolo[4,5-d]pyrimidine-2,7(6H)-dione as the active component in a pharmaceutical composition.

Additionally in accordance with the invention, 5-amino-3-$\beta$-D-ribofuranosylthiazolo[4,5-d]pyrimidine-2,7(6H)-dione is utilized to enhance lymphocyte cells in a host by administering to the host a therapeutically effective amount of 5-amino-3-$\beta$-D-ribofuranosylthiazolo[4,5-d]pyrimidine-2,7(6H)-dione as the active component in a pharmaceutical composition.

Additionally in accordance with the invention a therapeutical pharmaceutical composition is disclosed which contains as its active ingredient a therapeutically effective amount of 5-amino-3-β-D-ribofuranosyl-thiazolo[4,5-d]pyrimidine-2,7(6H)-dione.

Additionally in accordance with the invention a prophylactic pharmaceutical composition is disclosed which contains as its active ingredient a prophylactically effective amount of 5-amino-3-β-D-ribofuranosyl-thiazolo[4,5-d]pyrimidine-2,7(6H)-dione. In addition the prophylactic composition can include a further antiviral agent as a further active ingredient.

Since as antitumor and antimetastatic agents the compounds of the invention stimulate various natural immune system responses, the compounds of the invention would be useful against a broad spectrum of tumors including but not necessary limited to carcinomas, sarcomas and leukemias. Included in such a class are mammary, colon, bladder, lung, prostate, stomach and pancreas carcinomas and lymphoblastic and myeloid leukemias.

The method of treating tumors is effective in bringing about regression, palliation, inhibition of growth, inhibition of metastasis and remission of tumors.

In an advantageous process of the invention the compounds of the invention are prepared by silylating a derivative of a 2,5,7-substituted thiazolo[4,5-d]pyrimidine and reacting said silyl derivative with a 1-O-substituted-blocked-D-pentofuranose in the presence of a catalyst to form a blocked nucleoside. The blocking groups can further be removed from said nucleoside. Additionally the nucleoside can be phosphorylated. The substituent groups on said 2,5,7-substituted thiazolo[4,5-d]pyrimidine are selected from the group consisting of H, halogen, —$NH_2$, —OH, =O and =S. For certain compounds of the invention the substituted blocked pentofuranosyl sugar is selected as a 1-O-acetyl-2,3,5-tri-O-acyl-D-pentofuranose particularly 1-O-acetyl-2,3,5-tri-O-benzoyl-D-ribofuranose.

DETAILED DESCRIPTION OF THE INVENTION

The synthesis of the guanosine analog, 5-amino-3-β-D-ribofuranosylthiazolo[4,5-d]pyrimidine-2,7(6H)-dione, can be effected by the direct glycosylation of the preformed guanine base analog. (Scheme I). Thus, 5-aminothiazolo[4,5-d]pyrimidine-2,7(3H,6H)-dione (4), prepared in five steps from the commercially available diaminopyrimidinone by the method of Baker and Chatfield, *J. Chem. Soc.* (C), 2478 (1970), was glycosylated by trimethylsilylation using hexamethyldisilazane followed by treatment with 1-O-acetyl-2,3,5-tri-O-benzoyl-D-ribofuranose (5) in the presence of trimethylsilyl trifluoromethanesulfonate as a catalyst. The major product, 5-amino-3-(2,3,5-tri-O-benzoyl-β-D-ribofuranosyl)thiazolo[4,5-d]pyrimidine-2,7(6H)-dione (6) was isolated.

Treatment of 6 with sodium methoxide in methanol gave the deprotected guanosine analog, 5-amino-3-β-D-ribofuranosylthiazolo[4,5-d]pyrimidine-2,7(6H)-dione (7). When 7 was deaminated with excess nitrous acid the xanthosine analog, 3-β-D-ribofuranosylthiazolo[4,5-d]pyrimidine-2,5,7(4H,6H)-trione (8) was produced. Replacement of the 5-amino group of compound 6 by a hydrogen atom was accomplished by treatment of 6 with t-butyl nitrite in tetrahydrofuran to yield 3-(2,3,5-tri-O-benzoyl-β-D-ribofuranosyl)thiazolo[4,5-d]pyrimidine-2,7(6H)-dione (9). Deprotection of 9 using sodium methoxide in methanol or methanolic ammonia provided the inosine analog, 3-β-D-ribofuranosylthiazolo[4,5-d]pyrimidine-2,7(6H)-dione (10).

The guanosine analog, 7, was phosphorylated and the 5′-monophosphate (11) was obtained. The 3′,5′-cyclic monophosphate derivative, 12, was then prepared from 11.

The preparation of the analogous 8-mercapto compound in the thiazolo[4,5-d]pyrimidine system is depicted in Scheme II starting with 5-amino-2-chloro-thiazolo[4,5-d]pyrimidin-7(6H)-one (13). Compound 13 was treated with NaSH in ethylene glycol at 110° to provide the 2-thioxo heterocycle, 14. Glycosylation of 14 by the same procedure as that used to prepare the 2-oxo compound, 6, (except that some heating was required to ensure that any S-glycoside formed would be converted to the more thermodynamically stable N-glycoside) resulted in the formation of 5-amino-2-thioxo-3-(2,3,5-tri-O-benzoyl-β-D-ribofuranosyl)-thiazolo[4,5-d]pyrimidin-7(6H)-one (15). Treatment of 15 with sodium methoxide in methanol yielded the 8-mercaptoguanosine analog, 5-amino-2-thioxo-3-β-D-ribofuranosylthiazolo[4,5-d]pyrimidin-7(6H)-one (16).

Various related derivatives in the guanosine analog series were also prepared. The 6-thioguanosine analog was prepared by two routes starting from 6 (Scheme III). In one approach, 6 was treated with the mild chlorinating agent dimethyl(chloromethylene)ammonium chloride (generated in situ from thionyl chloride and DMF), and provided 5-amino-7-chloro-3-(2,3,5-tri-O-benzoyl-β-D-ribofuranosyl)thiazolo[4,5-d]pyrimidin-2-one(17). Reaction of 17 with thiourea in refluxing ethanol gave the protected thioguanosine analog, 5-amino-7(6H)-thioxo-3-(2,3,5-tri-O-benzoyl-β-D-ribofuranosyl)thiazolo[4,5-d]pyrimidin-2-one (18). Compound 18 was also prepared directly from 6 by reaction with $P_2S_5$ in pyridine. Deprotection of 18 was accomplished either with sodium methoxide in methanol or with methanolic ammonia and the 6-thioguanosine analog, 5-amino-7(6H)-thioxo-3-β-D-ribofuranosylthiazolo[4,5,-d]pyrimidin-2-one (19) was isolated as the crystalline monohydrate. The chloro function at position 7 was also nucleophilically substituted by azide using sodium azide in dry DMF which subsequently ring closed onto N-6 to form the new tricyclic ring compound, 5-amino-7-(2,3,5-tri-O-benzoyl-β-D-ribofuranosyl)tetrazolo[1,5-c]thiazolo[4,5-d]pyrimidin-2-one (20).

In an effort to study the thiazolo[4,5-d]pyrimidine ring system with respect to the order of nucleophilic substitution at the 2,5, and 7 positions and possibly use this information to synthesize the adenosine analog, chlorination of the readily available 2-chloro-thiazolo[4,5-d]pyrimidine-5,7(4H,6H)-dione (21) using refluxing $POCl_3$ and N,N-dimethylaniline (Scheme IV) was effected. The desired 2,5,7-trichlorothiazolo[4,5,-d]pyrimidine (22) was obtained along with a small amount of 5,7-dichloro-2-(N-methylanilino)-thiazolo[4,5-d]pyrimidine (23). The trichloro compound, 22, was carefully hydrolyzed in 1N NaOH at 60° C. in order to obtain the mono-oxo derivative, 5,7-dichlorothiazolo[4,5-d]pyrimidin-2(3H)-one (24), the structure of which was verified by single crystal X-ray analysis. Reaction of 24 with 1,2,3,5-tetra-O-acetyl-D-ribofuranose (25) under fusion glycosylation conditions produced 5,7-dichloro-3-2,3,5-tri-O-acetyl-β-D-ribofuranosyl)thiazolo[4,5-d]pyrimidin-2-one (26). Attempts to use 26 for further modification to obtain the adenosine analog were unsuccessful due to the labile nature of the thiazole ring toward nucleophilic ring-opening.

This was circumvented by the synthesis of the adenosine analog from its preformed heterocycle in the same manner as that used to obtain the guanosine analog. The known 2,7-diaminothiazolo[4,5-d]pyrimidine (27) served as the starting material (Scheme V). Treatment of 27 with nitrous acid under conditions similar to those used to prepare 13 provided 7-amino-2-chloro-thiazolo[4,5-d]pyrimidine (28). The structure of compound 28 was verified by single-crystal X-ray analysis. Treatment of 28 with NaSH in DMF at 0° C. yielded the 2-mercapto derivative, 7-aminothiazolo[4,5-d]pyrimidine-2(3H)-thione (29). The conversion of the 2-thioxo function in 29 to a 2-oxo function was accomplished using cold alkaline hydrogen peroxide to yield 7-aminothiazolo[4,5-d]pyrimidin-2(3H)-one (30). Reaction of 30 with the benzoyl-protected sugar, 5, under the same glycosylation conditions (at room temperature) as used to produce the blocked guanosine analog, 6, resulted in the formation of the unexpected blocked 4-ribofuranosyl isomer, 7-amino-4-(2,3,5-tri-O-benzoyl-$\beta$-D-ribofuranosyl)thiazolo[4,5-d]pyrimidin-2(3H)-one (31), as the only isomer detected and isolated. If, however, the same reaction was carried out at elevated temperature (80° C.), the predominant product obtained was the desired 3-ribofuranosyl isomer, 7-amino-3-(2,3,5-tri-O-benzoyl-$\beta$-D-ribofuranosyl)thiazolo[4,5-d]pyrimidin-2-(3H)-one (32). Both isomers, 31 and 32. were deprotected using sodium methoxide in dry methanol to obtain 7-amino-4-$\beta$-D-ribofuranosyl-thiazolo[4,5-d]pyrimidin-2(3H)-one (33) and 7-amino-3-$\beta$-D-ribofuranosylthiazolo[4,5-d]pyrimidin-2(3H)-one (34), respectively.

The 2'-deoxyerythropentofuranosyl, the xylofuranosyl and the arabinofuranosyl analogs of compound 7 can be prepared in a manner similar to that described for compound 7 (scheme VI). Thus reacting 4 with 1-chloro-2-deoxy-3,5-di-O-(p-toluoyl)-$\alpha$-D-erythropentofuranose followed by deblocking yields 5-amino-3-(2-deoxy-$\beta$-D-erythropentofuranosyl)thiazolo[4,5-d]pyrimidine-2,7(3H,6H)-dione (36). Likewise after deblocking of the respective intermediates, 4 and 1,2,3,5-tetra-O-acetyl-D-xylofuranose will yield 5-amino-3-($\beta$-D-xylofuranosyl)thiazolo[4,5-d]pyrimidine-2,7(3H,6H)-dione (38) and 4 and 1-chloro-2,3,5-tri-O-benzyl-$\alpha$-D-arabinofuranose will yield 5-amino-3-($\beta$-D-arabinofuranosyl)thiazolo[4,5-d]pyrimidine-2,7(3H,6H)-dione (40). The tri-O-acetyl (40) prodrug form of compound 7 is prepared from 4 and 1,2,3,5-tetra-O-acetyl-D-ribofuranose and the 2,3-di-O-isopropylidene derivative (42) is prepared directly from 7 (scheme VI).

For the compounds of the invention, pharmaceutically acceptable acid addition salts of the basic moiety can be selected from, but not necessarily limited to, the group consisting of hydrochloride, hydrobromide, hydroiodide, citrate, sulfate, substituted sulfate, phosphate, carbonate, bicarbonate and formate. Pharmaceutically acceptable salts of the phosphate moiety can be selected from, but not necessarily limited to, the group consisting of alkali and alkaline earths, e.g. sodium, potassium, calcium, magnesium, lithium, ammonium and substituted ammonium, trialkylammonium, dialkylammonium, alkylammonium, e.g. triethylammonium, trimethylammonium, diethylammonium, octylammonium, cetyltrimethylammonium and cetylpyridium.

The hydroxyl groups on the glycon and heterocycle and the amino groups of the heterocycle can be blocked with groups such as, but not necessarily limited to, acyl, isopropylidene and dimethylaminomethylene. The acyl group can be selected from a group consisting of $C_1$-$C_{18}$ straight chain, branched chain, substituted, unsaturated, saturated or aromatic acid such as, but not necessarily limited to acetic, trifluoroacetic, propionic, n-butyric, isobutyric, valeric, caproic, pelargonic, enanthic, caprylic, lactic, acrylic, propargylic, palmitic, benzoic, phthalic, salicylic, cinnamic and naphthoic acids.

Melting points were taken on a Thomas-Hoover capillary melting point apparatus or on a Haake-Buchler digital melting point apparatus and are uncorrected. Nuclear magnetic resonance ($^1$H NMR) spectra were determined at 300.1 MHz with an IBM NR300AF spectrometer. The chemical shifts are expressed in $\delta$ values (parts per million) relative to tetramethylsilane as internal standard. Ultra violet spectra (UV: sh=shoulder) were recorded on a Beckman DU-50 spectrophotometer. Elemental analyses were performed by Robertson Laboratory, Madison, N.J. Evaporations were carried out under reduced pressure with the bath temperature below 40° C. Thin layer chromatography (TLC) was run on silica gel 60 F-254 plates (EM Reagents). E. Merck silica gel (230–400 mesh) was used for flash column chromatography.

EXAMPLE 1

5-amino-3-(2,3,5-tri-O-benzoyl-$\beta$-D-ribofuranosyl)-thiazolo-[4,5-d]pyrimidine-2,7(6H)-dione (6)

A mixture of dry 5-aminothiazolo[4,5-d]pyrimidine-2,7-(3H,6H)-dione 4 (5.5 g, 30 mmol), hexamethyldisilazane (HMDS, 100 mL), ammonium sulfate (15 mg) and pyridine (10 mL) was heated under reflux for 4 h with the exclusion of moisture. Excess HMDS was removed by distillation to provide the syrupy bis-silyl derivative. The bis-silyl intermediate was dissolved in dry acetonitrile (300 mL) and 1-O-acetyl-2,3,5-tri-O-benzoyl-D-ribofuranose (5: 15.1 g, 30 mmol) was added followed by trimethlsilyl trifluoromethanesufonate (9.3 mL, 42 mmol). The clear reaction mixture was stirred at ambient temperature for 16 h. The solvent was evaporated to dryness and the residual syrup was dissolved in EtOAc (600 mL). The solution was washed with 5% $NaHCO_3$ solution (2×150 mL), and the dried ($Na_2SO_4$) organic layer was evaporated. The residual syrup was triturated with ether to yield 18.1 g (96%). The resulting foam was purified on a silica gel column by Prep LC techniques using $CHCl_3$-MeOH (9:1, v/v) as the solvent. Recrystallization of the residue from EtOH gave 5-amino-3-(2,3,5-tri-O-benzoyl-$\beta$-D-ribofuranosyl)-thiazolo[4,5-d]pyrimidine-2,7(6H)-dione (6) as colorless cyrstals: yield 14.5 g, 77%: mp 248°–250° C.: UV $\lambda_{max}$ (pH 1) 215 sh nm ($\epsilon$ 28000), 219 (28000), 224 sh (27,600), 301 (8500): UV $\lambda_{max}$ (pH 7) 215 sh nm ($\epsilon$ 28,900), 222 (29,500), 301 (10,600): UV $\lambda_{max}$ (pH 11) 218 nm ($\epsilon$ 27,800), 273 (6900): Anal. Calcd. for $C_{31}H_2N_4O_9S$: C, 59.23: H, 3.85: N, 8.91: S, 5.10. Found: C, 59.26: H, 3.89: N, 8.93: S, 5.23.

EXAMPLE 2

5-Amino-3-$\beta$-D-ribofuranosylthiazolo[4,5-d]pyrimidine-2,7(6H)-dione (7)

A solution of 6 (0.75 g, 1 mmol) in methanol (75 mL) was adjusted to pH 9 with $NaOCH_3$ and stirred at room temperature for 16 h. The reaction mixture was evaporated to dryness and the residue was triturated with ether (2×75 mL). The ether insoluble solid was dissolved in water (15 mL) and acidified with acetic acid whereupon the crude product precipitated. Crystallization of this material from water gave a colorless powder: yield 0.31 g, 78%: mp 238° C. (decomp.): UV $\lambda_{max}$ (pH 1) 215 nm ($\epsilon$ 2280), 245 (6900), 301 (8400): UV $\lambda_{max}$ (pH 7) 215 nm ($\epsilon$ 22,100), 245 (6900), 301 (8000): UV $\lambda_{max}$ (pH 11) 245 nm ($\epsilon$ 5700), 291 (6000). NMR (DMSO-d$_6$) $\delta$ 5.79 (1H, d, J=5.32 Hz, C$_1$, H), 6.90 (2H, s, NH$_2$), 11.12 (1H, s, NH), and other sugar protons. Anal Calcd. for C$_{10}$H$_{12}$N$_4$O$_6$S.H$_2$O: C, 35.92: H, 4.22: N, 16.76: S, 9.59. Found: C, 35.82: H, 4.02: N, 16.92: S, 9.66.

EXAMPLE 3

3-$\beta$-D-Ribofuranosylthiazolo[4,5-d]pyrimidine-2,5,7(4H,6H)-trione (8)

To a suspension of 7 (0.76 g, 2.4 mmol) in glacial acetic acid (150 mL) was added dropwise a solution of sodium nitrite (1.5 g, 21.7 mmol) in water (15 mL) with stirring. After 30 min the suspension became clear and stirring was continued at room temperature overnight. The white solid which had separated was filtered, washed with cold water and dried. Recrystallization from hot water gave fine colorless crystals of 8: yield 0.3 g, 40%: mp 250° C. dec.: UV $\lambda_{max}$ (pH 1) 293 nm ($\epsilon$ 5500): UV $\lambda_{max}$ (pH 7) 212 nm ($\epsilon$ 14,200), 301 (6100): UV $\lambda_{max}$ (pH 11) 204 nm ($\epsilon$ 21,900), 301 (5600). Anal Calcd. for C$_{10}$H$_{11}$N$_3$O$_7$S: C, 37.86: H, 3.49: N, 13.24: S, 10.10. Found: C, 37.81: H, 3.42: N, 13.01: S, 10.01.

EXAMPLE 4

3-(2,3,5-Tri-O-benzoyl-$\beta$-D-Ribofuranosyl)-thiazolo[4,5-d]pyrimidine-2,7(6H)-dione (9)

To a solution of 6 (6.65 g, 10.6 mmol) in dry THF (350 mL) was added ter-butyl nitrite (6.2 mL, 52.3 mmol) and the mixture was stirred at room temperature for 1 h. Additional nitrite reagent (2.0 mL) was added and the mixture was stirred at 50°-60° C. overnight. The mixture was evaporated and the residue was purified by flash column chromatography on silica gel using 8-10% acetone in CH$_2$Cl$_2$ followed by 10-11%. The desired product eluted last to yield 3.45 g (46%) of 9 as a foam: UV $\lambda_{max}$ (EtOH) 220 nm ($\epsilon$ 46600), 259 sh (11000), 271 sh (8400): 1H NMR (DMSO-d$_6$) $\delta$ 6.31 (d, J=6.45 Hz, 1H, C$_1$, H), 7.38-7.98 (m, 15H, benzoyl aromatics), 8.25 (s, 1H, C$_5$H), 13.16 (b, 1H, N$_6$H, exchanged with D$_2$O), and other sugar protons.

EXAMPLE 5

3-$\beta$-D-Ribofuranosylthiazolo[4,5-d]pyrimidine-2,7(6H)-dione (10)

Compound 9 (1.0 g, 1.63 mmol) was combined with methanolic ammonia (saturated at 0° C., 50 mL) and heated at 90° C. for 14 h in a steel bomb. The solvent was evaporated and the residue was treated with hot benzene which was decanted off. The resulting solid was purified by silica gel flash chromatography using chloroform and then CHCl$_3$-MeOH (6:1) to yield 280 mg (57%) of 10 after crystallization from water: mp 216°-218° C.: UV $\lambda_{max}$ (pH 1) 217 nm ($\epsilon$ 25,300), 259 (9700), 286 (6300): 1H NMR (DMSO-d$_6$) $\delta$ 5.85 (d, J=5.1 Hz, 1H, C$_1$, H), 8.30 (s, 1H, C$_5$H), 13.09 (b, 1H, N$_6$H, exchanges with D$_2$O), and other sugar protons.

Anal. Calcd. for C$_{10}$H$_{11}$N$_3$O$_6$S: C, 39.87: H, 3.68: N, 13.95: S, 10.64. 3.61: N, 14.06: S, 10.43.

EXAMPLE 6

3-$\beta$-D-Ribofuranosylthiazolo[4,5-d]pyrimidine-2,7(6H)-dione 5'-Monophosphate Ammonium Salt (11)

To a suspension of (2.1 g, 6.6 mmol) in freshly distilled trimethyl phosphate (25 mL) at −20° C. was added POCl$_3$ (0.64 mL, 6.6 mmol) and then an additional equivalent of POCl$_3$ after 1 h. The mixture was stirred at −5° C. for another 2 h and then poured into ethyl ether (150 mL, anhydrous) and centrifuged (6000 rpm, 10 min). The ether layer was decanted and ice water (100 mL) was added to the residual oil. The pH of the resulting solution was adjusted to 7.5 with aqueous ammonium bicarbonate and the solution was applied to a DEAE-cellulose column (3.2×35 cm), washed with water and eluted with a gradient (0 to 0.25 M, 2 L reservoirs) of aqueous ammonium bicarbonate. During the water wash, unreacted starting material eluted off (0.5 g). The appropriate fractions were pooled, evaporated and lyophilized several times to yield 1.01 g (48%, based on reacted starting material): mp 190°-194° C. UV $\lambda_{max}$ (pH 1,7) 243 nm ($\epsilon$), 301 ( ): UV $\lambda_{max}$ (pH 11) 243 nm ($\epsilon$), 289 ( ): 1H NMR (DMSO-d$_6$) $\delta$ 5.71 (s, 1H, C$_1$,H), 7.15 (b, 5H, NH$_2$ and NH$_4$+, exchanges with D$_2$O), 11.25 (b, 1H, N$_6$H, exchanges with D$_2$O), and other sugar protons. Anal. C$_{10}$H$_{14}$N$_5$O$_8$SP.1.25H$_2$O: C, 28.75: H, 3.98: N, 16.76: S, 7 67: P, 7.41. Found: C, 29.15: H, 3 68: N, 16 39: S, 7.76: P, 7.22.

EXAMPLE 7

5-Amino-3-$\beta$-D-Ribofuranosylthiazolo4,5-d]pyrimidine-2,7(6H)-dione 3',5'-Cyclic Monophosphate Ammonium Salt (12)

Compound 11 (1.02 g, 2.28 mmol) was dissolved in water (10 mL) and pyridine (3 mL) and morpholinodicyclohexylcarbodiimide (667 mg, 2.28 mmol) was added. The solution was evaporated and co-evaporated to a syrup several times with dry pyridine. After drying overnight over P$_2$O$_5$ under vacuum, the syrup was dissolved in dry pyridine (100 mL) and added dropwise to a refluxing solution of pyridine (300 mL) containing DCC (25 g). The solution was refluxed for an additional 2 h, cooled and allowed to stir overnight. The mixture was evaporated to dryness and the residue was partitioned between water (150 mL) and ethyl ether (150 mL). The aqueous layer was concentrated to about 100 mL and applied, having pH 7.7, to a DEAE-cellulose column (3.2×30 cm) and washed with water followed by elution using a gradient of aqueous ammonium bicarbonate (0 to 0.19 M). The proper fractions were collected based on UV monitoring, evaporated and lyophilized several times to yield 190 mg (22%) of the title compound: mp 244° C. (dec.): UV $\lambda_{max}$ (pH 1,7) 243 nm ($\epsilon$), 300 ( ): UV $\lambda_{max}$ (pH 11) 243 nm ($\epsilon$), 289 ( ): 1H NMR (DMSO-d$_6$) 5.60 (d, J 4.44, 1H, 2'OH, exchanges with D$_2$O), 5.72 (s, 1H, C$_1$, H), 7.15 (b, 6H, NH$_2$ and NH$_4$, exchanges with D$_2$O), 11.40 (b, 1H, N$_6$H, exchanges with D$_2$O), and other sugar protons. Anal. Calcd. for C$_{10}$H$_{11}$N$_4$O$_8$SP.NH$_3$.1.25H$_2$O: C, 28.75: H, 3.98: N, 16. Found: C, 29.15: H, 3.68: N, 16.39: S, 7.76: P, 7.22.

EXAMPLE 8

5-Amino-2-thioxothiazolo[4,5-d]pyrimidin-7(6H)-one (14)

A suspension of 5-amino-2-chlorothiazolo[4,5-d]pyrimidin-7(6H)-one (13: 1 5 g, 7.4 mmol) in ethylene glycol (30 was heated to 110° C. and $NaSH_xH_2O$ (420 mg, 74 mmol) was added. A clear solution was not obtained, however, until an additional 250 mg were added. The clear solution was stirred at 110° C. for 2 h and then the reaction mixture was cooled to room temperature, poured into ice (300 mL), and the pH adjusted to 2-3 with 10% HCl. The resulting pink gelatinous mixture was boiled for 1 h and the pink solid was collected by filtration through a medium frit-glass filter, washed with water and dried: yield 1.2 g, 81%: an analytical sample was prepared by flash column chromatography using $EtOAc-MeOH-H_2O$-acetone (7:1:1:1). mp>300° C.: UV $\lambda_{max}$ (pH 1) 243 nm ($\epsilon$13,700), 266 (16,500), 351 (17,200) UV $\lambda_{max}$ (pH7) 262 nm ($\epsilon$ 14,800), 345 (12,700): UV $\lambda_{max}$ (pH 11) 250 nm ($\epsilon$ 19,300), 335 (14,300): $^1$H NMR (DMSO-$d_6$) $\delta$ 6.91 (s, 2H, $NH_2$), 11.18 (s, 1H, $N_6H$), 13.78 (s, 1H, $N_3H$).

EXAMPLE 9

5-Amino-2-thioxo-3-(2,3,5-tri-O-benzoyl-$\beta$-D-ribofuranosyl)-thiazolo[4,5-d]pyrimidin-7(6H)-one (15)

Compound 14 (1.0 g, 5 mmol) was glycosylated in the same manner as that used to prepare 6, requiring HMDS (20 mL), benzoyl-blocked sugar (5: 2.52 g, 5 mmol), and TMS-triflate (1.45 mL, 7.5 mmol). At the end of the 16 h reaction period, the reaction mixture was heated at 70° C. for 3 h in order to rearrange any S-glycoside formed to the more stable N-glycoside. After the same workup, 15 (2.1 g crude) was purified by flash column chromatography using hexanesacetone (1:1) and crystallized from toluene-EtOAc: yield 1.9 g, 59%: mp 230°-233° C. (darkens 195° C.). Anal. Calcd. for $C_{31}H_{24}N_4O_8S_2$: C, 57.76: H, 3.75: N, 8.69: S, 9.95. Found: C, 57.98: H, 3.46: N, 8.40: S, 9.66.

EXAMPLE 10

5-Amino-2-thioxo-3-$\beta$-D-ribofuranosylthiazolo[4,5-d]pyrimidin-7(6H)-one (16)

To a solution of 15 (1.25 g, 1.94 mmol) in dry methanol (100 mL) was added sodium methoxide powder until the pH reached 10. The solution was stirred overnight and then neutralized with Dowex H$^+$ resin and filtered. After evaporation of the filtrate, the residue was washed with ether to remove methyl benzoate and the crude material was crystallized from water: yield 520 mg, 81%: mp 220° C. dec.: UV $\lambda_{max}$ $^1$H NMR (DMSO-$d_6$) $\delta$ 6.48 (d, J=3.00 Hz, 1H, $C_1$,H), 6.99 (s, 2H, $NH_2$), 11.47 (s, 1H, NH), and other sugar protons. Anal. Calcd. for $C_{10}H_{12}N_4O_5S_2.H_2O$: C, z34.28: H, 4.03: N, 15.99: S, 18.30. Found: C, 33.99: H, 3.92: N, 15.68: S, 18.22.

EXAMPLE 11

5-Amino-7-chloro-3-(2,3,5-tri-O-benzoyl-$\beta$-D-ribofuranosyl)thiazolo[4,5-d]pyrimidin-2-one (17)

Dry purified 6 (10 g, 16 mmol) was dissolved in dry methylene chloride (350 mL) and a solution of freshly distilled thionyl chloride (40 mL), dry DMF (20 mL), in dry methylene chloride was added dropwise over a 2 h period and the reaction was kept at 60° C. (reflux) for 16 h. The reaction mixture was poured carefully into ice and $NaHCO_3$ solution and stirred for 30 min. The layers were separated and the aqueous layer extracted (2×150 mL) with methylene chloride and the combined layers dried over $Na_2SO_4$ and evaporated in vacuo. The residual syrup was purified by passing through a silica gel column (4×40 cm) and eluting with $CHCl_3$-acetone (4:1), to obtain the chloro compound as a white foam, 8.6 g, 84%: mp 88°-90° C.: Anal. Clcd. for $C_{31}H_{23}C_1N_4O_8S$: C, 57.54: H, 3.58: $C_1$, 5.47: N, 8.66: S, 4.96. Found: C, 58.06: H, 3.99: Cl, 5.95: N, 9.41: S, 4.75.

EXAMPLE 12

5-Amino-7(6H)-thioxo-3-(2,3,5-tri-O-benzoyl-$\beta$-D-ribofuranosyl)thiazolo[4,5-d]pyrimidin-2-one (18)

Method 1. A mixture of 17 (3.3 g, 5 mmol), thiourea (0.719 g, 1 mmol) and EtOH (100 mL) was heated under reflux for 6 days. The reaction mixture was evaporated, and the residue was extracted with $CHCl_3$ (200 mL). The solvent was evaporated to dryness in vacuo, and the residue was purified by silica gel column chromatography with $CHCl_3$-acetone (7:1) as the eluant. After evaporation the residue was crystallized from EtOH to afford a colorless powder: yield 1.9 g, 58%: mp 227°-229° C.: UV $\lambda_{max}$ (pH 1) 234 nm ($\epsilon$ 26,000), 280 sh (9000), 365 (11,800): UV $\lambda_{max}$ (pH 11) 230 nm ($\epsilon$ 40,500), 267 (8700), 327 (14,100): Anal calcd. for $C_{31}H_{24}N_4O_8S_2$: C, 57.75: H, 3.75: N, 8.69: S, 9.95. Found: C, 57.79: H, 3.79: N, 8 69: S, 9.98.

Method 2. To a solution of 6 (1 g, 1.6 mmol) in pyridine (50 mL) was added with stirring $P_2S_5$ (1.5 g, 6.2 mmol). The solution was refluxed gently (bath temperature 130-140) for 29 h. The reaction mixture was evaporated to dryness in vacuo. The excess $P_2S_5$ was decomposed by the addition of $H_2O$ (200 mL) at 60° C. The mixture was stirred for 1 h, then left at room temperature overnight. The resulting solid was filtered, dissolved in $CHCl_3$, dried ($Na_2SO_4$) and the solvent removed under vacuum. The residue was purified by silica gel column chromatography with $CHCl_3$-acetone 7:1 as the eluant. After concentration the residue was crystallized from EtOH to give 18 (0.43 g, 43%). The physicochemical properties of compound 18 prepared by Method 2 were found to be identical in all respects to those of the compound prepared by Method 1 above.

EXAMPLE 13

5-Amino-7(6H)-thioxo-3-$\beta$-D-ribofuranoxyl-thiazolo[4,5-d]pyrimidin-2-one (19)

Method 1. A solution of 18 (1 g, 1.6 mmol) in methanol (50 mL) was adjusted to pH 9 with $NaOCH_3$ and stirred at room temperature for 16 h. The reaction mixture was evaporated to dryness and the residue was triturated with ether (2×75 mL). The ether insoluble solid was dissolved in water (15 mL) and acidified with acetic acid whereupon the crude product was precipitated. Recrystallization of this material from EtOH-$H_2O$ gave colorless prisms: yield 0.47 g, 87%: mp 185°-187° C.: UV $\lambda_{max}$ (pH 1) 214 nm ($\epsilon$ 2700), 230 sh (14,000), 263 (6700), 354 ( ): UV $\lambda_{max}$ (pH 7) 213 nm ($\epsilon$ 25,900), 247 (9100), 266 sh (7700), 334 (12,000), 353 (11,800): UV $\lambda_{max}$ (pH 11) 247 nm ($\epsilon$ 12300), 266 sh (8800), 327 (16,100): $^1$H NMR (DMSO-$d_6$) $\delta$ 5.76 (d, J 5.32 Hz, $C_1$,H), 7.22 (s, 2H, $NH_2$), 12.41 (s, 1H, NH), and other sugar protons Anal. Calcd. for $C_{10}H_{12}N_4O_5S_2.H_2O$: C, 34.28: H, 4.03: N, 15.99: S, 18.30. Found: C, 34.28: H, 3.99: N, 16.24: S, 18.51.

Method 2. A solution of 18 (1.0 g, 1.6 mmol) in methanolic ammonia (saturated at 0° C., 60 mL) was stirred at room temperature for 48 h. The solvent was evaporated to dryness and the residue was triturated with boiling benzene (2×100 mL). The benzene insoluble solid was crystallized from EtOH-H$_2$O to give 19 (0.36 g, 67%). The compound prepared by this method was identical to compound 19 prepared by Method 1 above, as judged by spectral and physical data.

EXAMPLE 14

5-Amino-7-(2,3,5-tri-O-benzoyl-$\beta$-D-ribofuranosyl)tetrazolo[1,5-c]thiazolo[4,5-d]pyrimidin-2-one (20)

To a solution of 17 (3.0 g, 4.6 mmol) in dry DMF (30 mL) was added sodium azide (0.3 g, 4.6 mmol) and the mixture was stirred at room temperature for 3 days. After evaporation of the solvent, the residue was dissolved in EtOAc (250 mL) and washed with water (2×50 mL), dried over sodium sulfate and evaporated. The resulting foam was purified by silica gel column chromatography using CHCl$_3$-acetone 7:1. The product was crystallized from EtOH to give a white powder: yield, 2.0 g, 67%: mp 112°–114° C.: IR showed no azide band in the region of 2100 to 2200 cm$^{-1}$: UV $\lambda_{max}$ (MeOH). Anal. Calcd. for C$_{31}$H$_{23}$N$_7$O$_8$S: C, 56.96: H, 3.55: N, 15.00: S, 4.91. Found: C, 57.19: H, 3.88: N, 15.26: S, 4.75.

EXAMPLE 15

2,5,7-Trichlorothiazolo[4,5-d]pyrimidine (22)

A mixture of 2-chlorothiazolo[4,5-d]pyrimidine-5,7(4H,6H)-dione (21, 15.8 g, 78 mmol), POCl$_3$ (220 ml) and N,N-dimethylaniline (12.3 g, 0.1 mmol) was refluxed for 3 h. The excess POCl$_3$ was removed under reduced pressure and the residue was poured into ice-water (500 mL) with stirring. The resulting aqueous solution was extracted with CHCl$_3$ (3×400 mL) and the organic layer was washed with water (2×400 mL), 0.1N NaOH (2×300 mL) and water (2×400 mL) successively and then dried over Na$_2$SO$_4$. Evaporation of the chloroform produced a residue which was purified by silica gel column chromatography using CHCl$_3$ to provide the title compound (22) after crystallization from EtOH. Yield 13.8g, 74%: mp. 121°–122° C.: UV $\lambda_{max}$ (pH 1,7,11) 296 nm ($\epsilon$ 10,800). Anal. Calcd. for C$_5$Cl$_3$N$_3$S: C, 24.97: Cl, 44.22: N, 17.48. Found: C, 25.02: Cl$_1$, 44.39: N, 17.37.

EXAMPLE 16

5,7-Dichlorothiazolo[4,5-d]pyrimidin-2(3H)-one (24)

A suspension of the trichloro compound (22: 3.0 g, 12 mmol) in 1N NaOH (35 mL) was heated at 60° C. for 1 h. The solution was treated with decolorizing carbon and then acidified with 10% aqueous HCl. The resulting precipitate was collected and reprecipitated from dilute base with glacial acetic acid to provide 24 as orange needles (1.38g, 50%): mp. 191°–192° C.: UV $\lambda_{max}$ (pH 1) 254 nm ($\epsilon$ 5,300), 290 (11,400): UV $\lambda_{max}$ (pH 7,11) 226 nm ($\epsilon$ 28,900), 300 (14,100). Anal. Calcd. for C$_5$HCl$_2$N$_3$OS: C, 27.04: H, 0.45: Cl, 31.93: N, 18.93. Found: C, 26.78: H, 0.61: Cl, 32.15: N, 18.66. Single crystal X-ray analysis of 24 showed the structure assignment to be correct.

EXAMPLE 17

5,7-Dichloro-3-(2,3,5-tri-O-acetyl-$\beta$-D-ribofuranosyl)-thiazolo[4,5-d]pyrimidin-2-one (26)

A finely powdered mixture of 24 (3.7 g, 16 mmol), 1,2,3,5-tetra-O-acetyl-D-ribofuranose (5.3 g, 16 mmol) and bis-(p-nitrophenyl)phosphate (20 mg) was heated at 170° C. for 10 min under reduced pressure. After cooling to room temperature the brown solid mass was dissolved in EtOAc (500 mL) and washed with saturated aqueous sodium bicarbonate (3×300 mL). The dried (Na$_2$SO$_4$) organic layer was evaporated to yield a syrup which was purified by silica gel column chromatography (4×40 cm) using toluene-EtOAc (5:1). The resulting syrup was crystallized from ethanol to give a colorless powder: yield 6.4 g, 80%: mp 125°–126° C.: $^1$H NMR (DMSO-d$_6$) $\delta$ 1.99, 2.06, 2.08 (3s, 9H, acetyl), 6.07 (d, J=3.40 Hz, 1H, C$_1$,H), and other sugar protons. Anal. Calcd. for C$_{16}$H$_{15}$Cl$_2$N$_3$O$_8$S: C, 40.01: H, 3.15: Cl, 14.76: N, 8.75: S, 6.68. Found: C, 40.20: H, 3 31: Cl, 14.79: N, 8.61: S, 6 66.

EXAMPLE 18

7-Amino-2-chlorothiazolo[4,5-d]pyrimidine (28)

To a suspension of 2,7-diaminothiazolo[4,5-d]pyrimidine (27: 16.3 g, 97.3 mmol) in water (200 mL) at 55° C. was added enough 1N NaOH (about 100 mL) to dissolve the starting material and sodium nitrite (8.0 g) was then added. This solution was then added dropwise over 30 min. to a solution containing con HCl (400 mL), water (100 mL) and LiCl (60 g) at 30° C. The resulting mixture was warmed to 45° C. for 15 min. and then hot water (1 L, 90°) was added. The reaction mixture was stirred overnight at room temperature, filtered to remove unreacted starting material and the filtrate was neutralized with solid NaOH to pH 4. The resulting solid was filtered off, washed with water and dried to yield 28: 5.38 g, 34%: recrystallization from water gave an analytical sample: mp>234° C. decomp.: UV $\lambda_{max}$ (pH 1) 228 nm ($\epsilon$), 296 ( ) UV $\lambda_{max}$ (pH 7) 232 nm ($\epsilon$), 298 ( ): UV $\lambda_{max}$ (pH 11) 227 nm ($\epsilon$), 300 ( ): $^1$H NMR (DMSO-d$_6$) $\delta$ 7.82 (b, 2H, NH$_2$, exchanges with D$_2$O), 8.41 (s, 1H, C$_5$H). Anal. Calcd. for C$_5$H$_3$N$_4$SCl.0.1H$_2$O: C, 31.87: H, 1.71: N, 29.74: S, 17.02: Cl, 18.82. Found: C, 31.71: H, 1.50: N, 29.35: S, 16.92: Cl, 19.54.

EXAMPLE 19

7-Aminothiazolo[4,5-c]pyrimidine-2(3H)-thione (29)

A suspension of compound 28 (1.11 g, 5.9 mmol) in dry DMF (10 mL) was cooled in an ice bath to 0° C. and NaSH$_x$H$_2$O (0.87 g, 11.8 mmol) was added. The resulting clear solution was stirred overnight at 0° C. and then at room temperature for 2 h. The reaction mixture was poured into ice (300 mL) and the pH adjusted to 3-4 with glacial acetic acid. The solid precipitate was filtered, washed with water and dried to yield 0.96 g (88%). An analytical sample was prepared by crystallization from DMF-water: mp>370° C.: UV $\lambda_{max}$ (pH 1) 248 nm ($\epsilon$), 263 ( ), 345 ( ): UV $\lambda_{max}$ (pH 7, 11) 228 nm ($\epsilon$), 258 ( ), 329 ( ): $^1$NMR (DMSO-d$_6$) $\delta$ 7.57 (b, 1H, NH$_2$, exchanges with D$_2$O), 8.23 (s, 1H, C$_5$H), 14.13 (b, 1H, N$_3$H, exchanges with D$_2$O). Anal. Calcd. for C$_5$H$_4$N$_4$S$_2$: C, 32.60: H, 2.19: N, 30.41: S, 34.81. Found: C, 32.97: H, 2.13: N, 30.29: S, 34.59.

EXAMPLE 20

7-Aminothiazolo[4,5-d]pyrimidin-2(3H)-one (30)

To a suspension of 29 (770 mg, 4.2 mmol) in water (30 mL) was added 1N NaOH (4.2 mL) and 30% $H_2O_2$ (1.0 mL) and the reaction was stirred for 1 h at room temperature. Additional peroxide (2.0 mL) and hydroxide (5.0 mL) were added and the mixture was stirred for 1 h at 70° C. The reaction mixture was filtered and the filtrate was neutralized with glacial acetic acid. The resulting precipitate was filtered off while still hot, washed with cold water and dried to yield 0.52 g (74%): mp >370° C. UV $\lambda_{max}$ (pH 1) 267 nm ($\epsilon$), 289 ( ): UV $\lambda_{max}$ (pH 7, 11) 285 nm ($\epsilon$): $^1$H NMR (DMSO-$d_6$) $\delta$ 7.18 (b, 2H, $NH_2$, exchanges with $D_2O$), 8.12 (s, 1H, $C_5H$), 12.30 (b, 1H, $N_3H$, exchanges with $D_2O$). Anal. Calcd. for $C_5H_4N_4OS$: C, 35.71: H, 2.40: N, 33.31: S, 19.07. Found: C, 35.50: H, 2.36: N, 33.13: S, 18.79.

EXAMPLE 21

7-Amino-4-(2,3,5-tri-O-benzoyl-$\beta$-D-ribofuranosyl)-thiazolo[4,5-d]pyrimidin-2-one (31)

Compound 30 (460 mg, 2.7 mmol) was glycosylated in the same manner as that used to prepare 6, requiring HMDS (30 mL), benzoyl-blocked sugar (5: 1.5 g, 3.0 mmol), and TMS-triflate (0.76 mL, 3.9 mmol). The reaction mixture was allowed to stir overnight at room temperature and was then worked up as described for 6 to yield 1.6 g (95%) of 31 isolated as a foam: UV $\lambda_{max}$ (MeOH) 230 nm ($\epsilon$), 310 ( ): $^1$H NMR (DMSO-$d_6$) $\delta$ 6.45 (d, J=2.73 Hz, 1H, $C_1H$), 7.4–8.0 (m, 15H, benzoyl aromatics), 8.59 (s, 1H, $C_5H$), and other sugar protons. $C_{31}H_{24}N_4O_8S$: C, 60.78: H, 3.95: N, 9.15: S, 5.23. Found:

EXAMPLE 22

7-Amino-3-(2,3,5-tri-O-benzoyl-$\beta$-D-ribofuranosyl)-thiazolo[4,5-d]pyrimidin-2-one (32)

Compound 30 (1.22 g, 7.25 mmol) was glycosylated as described for the preparation of 6, requiring HMDS (35 mL), benzoyl-blocked sugar (5: 4.4 g, 8.7 mmol) and TMS-triflate (2.0 mL, 10.3 mmol). After stirring overnight at room temperature, the reaction mixture was refluxed for 2 days and then worked up in the usual manner. The crude mixture was subjected to flash silica gel column chromatography using a gradient of methylene chloride to methylene chloride-acetone 10:1 (v/v) and yielded two products. The first to elute from the column was assumed by $^1$H NMR to be a bis-glycoside which amounted to 660 mg. The second and major product off the column was obtained as a foam and assigned as the desired 3-ribosyl isomer by UV and $^1$H NMR: yield 1.04 g (24%): UV $\lambda_{max}$ (EtOH) 232 nm ($\epsilon$), 283 ( ): $^1$H NMR (DMSO-$d_6$) $\delta$ 6.34 (t, 1H, $C_1H$), 7.39–7.98 (m, 17H, benzoyl aromatics and $NH_2$, 8.19 (s, 1H, $C_5H$), and other sugar protons. Anal. Calcd. for C, 60.78: H, 3.95: N, 9.15: S, 5.23. Found: 3.93: N, 8.13: S, 4.85.

EXAMPLE 23

7-Amino-4-$\beta$-D-ribofuranosylthiazolo[4,5-d]pyrimidin-2-one (33)

Compound 31 (310 mg, 0.51 mmol) was dissolved in dry methanol (35 mL) and cooled to 5° C. To this solution was added solid sodium methoxide (82 mg, 1.5 mmol) and the solution was stirred at room temperature for 5 h. The mixture was neutralized with Dowex-50 H$^+$ resin, filtered and evaporated to dryness. The residue was triturated with ethyl ether and then recrystallized from aqueous ethanol to yield colorless needles: 120 mg, 80%: mp 132°–134° C.: UV $\lambda_{max}$ (pH 1) 227 nm ($\epsilon$ 17,230), 301 (15,750): UV $\lambda_{max}$ (pH 7, 11) 233 nm ($\epsilon$ 22,300), 305 (19,100): $^1$H NMR (DMSO-$d_6$) $\delta$ 5.96 (d, J=3.51 Hz, 1H, $C_1,H$), 7.75 (b, 2H, $NH_2$), and other sugar protons. Anal. Calcd. for $C_{10}H_{12}N_4O_5S \cdot O.2H_2O$: C, 35.71: 9.53. Found: C, 35.45: H, 4.88: N, 16.44: S, 9.50.

EXAMPLE 24

7-Amino-3-$\beta$-D-ribofuranosylthiazolo[4,5-d]pyrimidin-2-one (34)

Compound 32 (0.76 g, 1.2 mmol) was deblocked in the same manner as described for 31 above using sodium methoxide (200 mg, 3.7 mmol) in dry MeOH (50 mL). The title compound (34) was obtained (0.12, 32%) after crystallization from water: mp 248°–250° C.: UV $\lambda_{max}$ (pH 1) 222 nm ($\epsilon$ 35100), 265 (14,300), 290 (11,400): UV $\lambda_{max}$ (pH 7, 11) 215 nm ($\epsilon$ 45000), 262 (13,200): $^1$H NMR (DMSO-$d_6$) $\delta$ 5.91 (d, J=5.43 Hz, 1H, $C_1,H$), 7.44 (b, 1H, $NH_2$), 8.22 (s, 1H, $C_5H$), and other sugar protons. Anal. Calcd. for $C_{10}H_{12}N_4O_5S$: C, 40.00: H, 4.03: N, 18.66: S, 10.68. Found: C, 39.80: H, 3.99: N, 18.39: S, 10.57.

EXAMPLE 25

5-Amino-3-(2-deoxy-3,5-di-O-(p-toluoyl)-$\beta$-D-erythropentofuranosyl)thiazolo[4,5-d]pyrimidin-2,7-dione (35)

5-Aminothiazolo[4,5-d]pyrimidin-2,7-dione (4.3 g, 23.3 mmol) was combined with trimethylsilyl trifluoromethanesulfonate (13.6 mL, 73.4 mmol) in hexamethyldisilazane (70 mL) and the mixture refluxed for three hours after which the excess solvent was removed by vacuum distillation. The resulting solid mass was combined with 1-chloro-2-deoxy-3,5-di-O-(p-toluoyl)-$\alpha$-D-erythro-pentofuranose (11.8 g, 73 mmol) and the mixture fused at 110° C. for 30 minutes. The resulting product was dissolved in EtOAc (400 mL) and poured into a stirring aqueous 5% NaHCO$_3$ solution. The organic phase was isolated, dried over anhydrous sodium sulfate, and purified by flash column chromatography (dichloromethane/acetone, 4:1 as eluant) to give 1.7g (14%) of a mixture of $\alpha$ and $\beta$ isomers; mp 268–270; UV $\lambda_{max}$ (pH 1) 243, 300 nm; UV $\lambda_{max}$ (pH 7) 243, 302 nm; UV $\lambda_{max}$ (pH 11) 243, 284 nm; $^1$H NMR (Me$_2$SO-$d_6$) $\sigma$ 6.37 (t,1,$C_1'H$) 7.0 (bs, 2, $NH_2$, exchanged with $D_2O$) 7.2 and 7.9 (m, 5, $CH_3C_6H_5$) 11.35 (bs, 1, $N_6H$, exchanged with $D_2O$) and other sugar protons. NMR seems to indicate only one isomer.

EXAMPLE 26

5-Amino-3-(2-deoxy-$\beta$-D-erythropentofuranosyl)-thiazolo[4,5-d]pyrimidine-2,7(3H,6H)-dione (36)

Sodium methoxide (120 mg, 2.2 mmol) was added to a solution of 5-Amino-3-(2-deoxy-3,5-di-O-(p-toluoyl)-$\beta$-D-erythropentofuranosyl)thiazolo[4,5-d]pyrimidin-2,7-dione (35; 0.465g, 0.87 mmol) in anhydrous methanol (100 mL) and the resulting solution stirred at room temperature for 8 hours. The solution was neutralized with Dowex 50W-X8 (H$^+$ form) resin, filtered, and evaporated to dryness and the residue treated with anhydrous ether (35 mL). After trituration, the suspension was decanted to give a dry powder which was crystallized (charcoal treatment, Norit A) from ethanol. After filtering off the initial precipitate, 110 mg (42%) of the β isomer could be recovered by fractional crystallization using ethanol. mp>170° C. (scinters), UV $^1$H NMR (Me2SO-d$_6$) σ4.68 (t, 1, J=5.7 Hz, C$_3'$OH, exchanged with D$_2$O), 5.20 (d, 1, J=3.9 Hz, C$_5'$OH, exchanged with D$_2$O), 6.24 (t, 1, J=7.2 Hz C$_1'$H), 6.94 (bs, 2, NH$_2$, exchanged with D$_2$O), 11.23 (bs, 1, N$_6$H, exchanged with D$_2$O); Anal. Calcd. for C$_{10}$H$_{12}$N$_4$O$_5$S: C, 40.00; H, 4.03; N, 18.66; S, 10.68; Found: C, 40.27; H, 3.92; N, 18.75; S, 10.42.

EXAMPLE 27

5-Amino-3-(β-D-xylofuranosyl)thiazolo[4,5-d]pyrimidine-2,7-(3H,6H)-dione (38)

The title compound is prepared by glycosylation of 4 exactly as described above for the synthesis of 6 except that 1,2,3,5-tetra-O-acetyl-D-xylofuranose is to be used. The crude acetyl-blocked nucleoside (37) is then deprotected using sodium methoxide as described for the preparation of 7 to yield 38 as an amorphous solid.

EXAMPLE 28

5-Amino-3-(2,3,5-tri-O-benzyl-β-D-arabinofuranosyl)-thiazolo[4,5-d]pyrimidine-2,7(3H,6H)-dione (39)

The title benzyl-protected nucleoside is prepared in the same manner as that described for 35 except that the sugar to be used, 1-chloro-2,3,5-tri-O-benzyl-α-D-arabinofuranose, is generated from the corresponding 1-O-(p-nitrobenzoyl) sugar using dry hydrogen chloride gas in dichloromethane at 0° C. The mixture of anomers is separated by flash silica gel column chromatography to yield 39 and its α anomer, both as dry foams.

EXAMPLE 29

5-Amino-3-(β-D-arabinofuranosyl)thiazolo[4,5-d]pyrimidine-2,7(3H,6H)-dione (40)

Compound 39 is dissolved in dry dichloromethane and deprotected using an excess of boron trichloride (1M in dichloromethane) at −78° C. and allowed to warm to −40° C. for 2 hours before quenching with methanol. The residue after workup is crystallized from water to yield 40 as a colorless crystalline solid.

EXAMPLE 30

5-Amino-3-(2,3,5-tri-O-acetyl-β-D-ribofuranosyl)-thiazolo[4,5-d]-pyrimidine-2,7(3H,6H)-dione (41)

Compound 4 (10 g, 54.4 mmol) was glycosylated exactly as described for the synthesis of 6 except that the sugar used in this case was the 1,2,3,5-tetra-O-acetyl-D-ribofuranose (20.7 g, 65.1 mmol). After the usual workup the crude residue was flash chromatographed on silica gel using 10% methanol in dichloromethane. Yield of pure material 7.1 g (29%) as a dry foam or amorphous solid.

EXAMPLE 31

5-amino-3-(2,3-di-O-isopropylidene-β-D-ribofuranosyl)thiazolo-[4,5-d]pyrimidine-2,7-dione (42)

To a ice-cold suspension of 5-amino-3-(β-D-ribofuranosyl)thiazolo[4,5-d]pyrimidine-2,7-dione (7; 1.86 g, 6 mmol) in a mixture of acetone (100 mL) and dimethoxypropane (150 mL) was added perchloric acid (1.0 mL) dropwise, and the resulting mixture stirred at 0° for 30 minutes. The reaction mixture was neutralized in cold to pH 7 with 1N sodium hydroxide. The resulting solution was concentrated in vacuo and the residue flash chromatographed on silica gel with 10% acetone in chloroform as eluent to yield the title compound as an amorphous solid.(1.7g, 80%). $^1$H NMR (DMSO d$_6$, 300 MHz): δ 1.28, 1.47 (2s, 6H, isopropylidene methyls),6.0 (d, 1H, C$_1$H), 7.0 (bs, 2H, NH$_2$), 11.29 (s, 1H, NH) and other sugar protons. Anal. Calcd. for C$_{13}$H$_{16}$N$_4$SO$_6$: C, 43.82; H, 4.53; N, 15.72; S, 9.00. Found: C, 43.65; H, 4.48; N, 15.41; S, 8.94.

SCHEME I

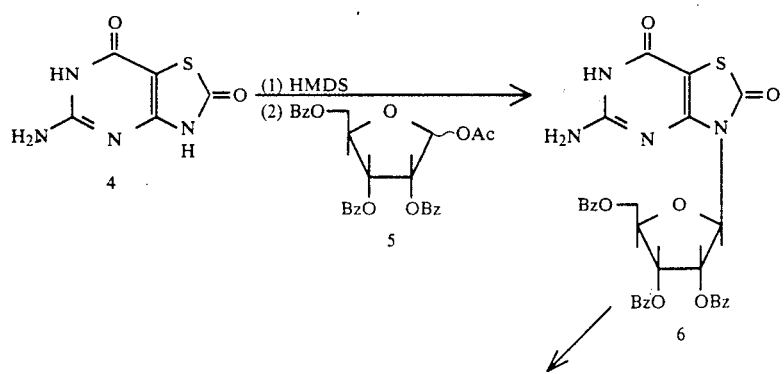

SCHEME I
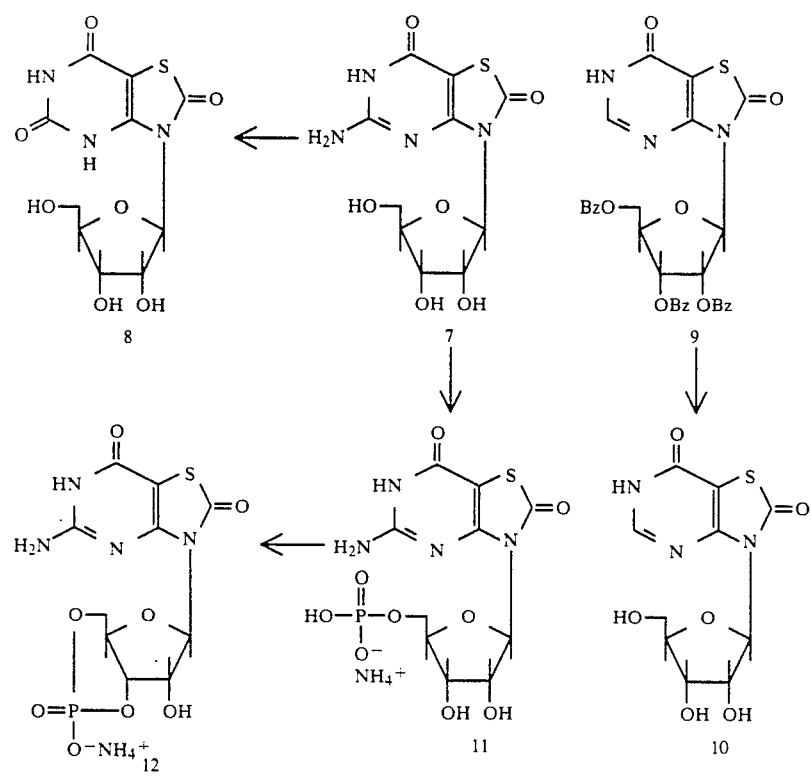
SCHEME II
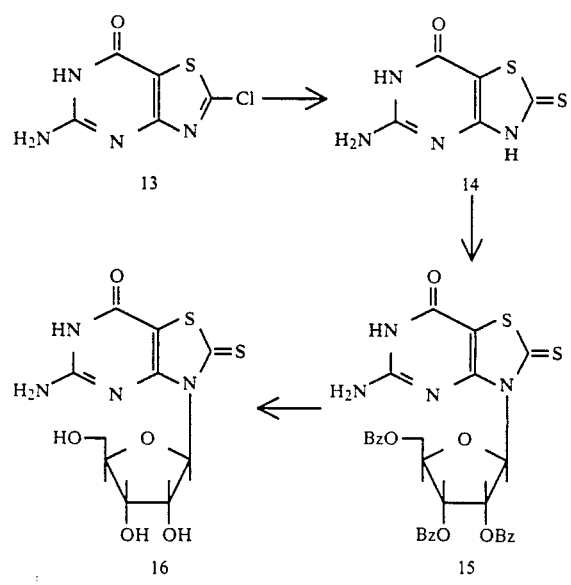
SCHEME III
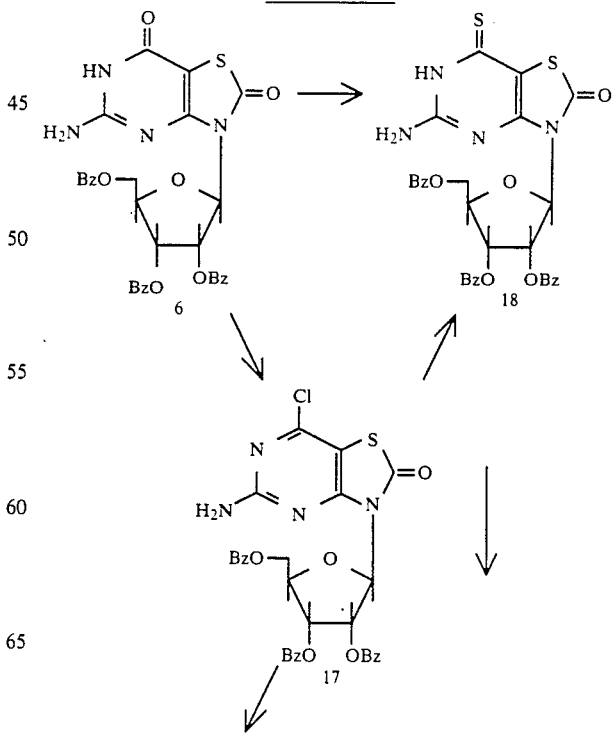

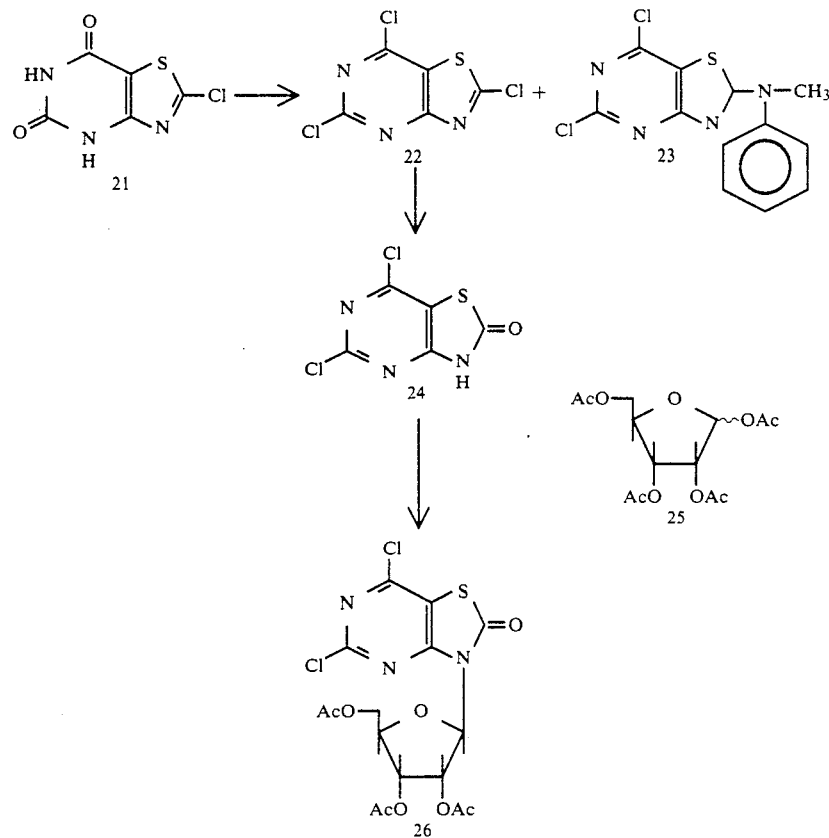
SCHEME IV
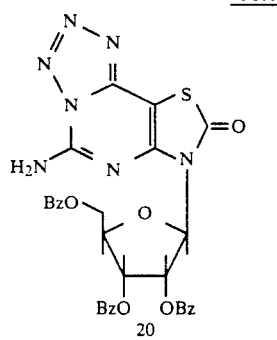
-continued
SCHEME III
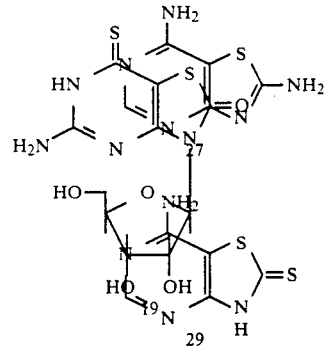
SCHEME V
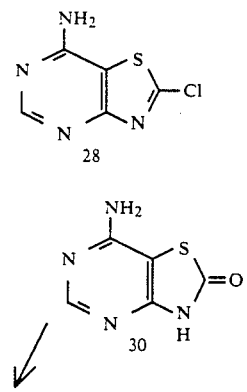

SCHEME V

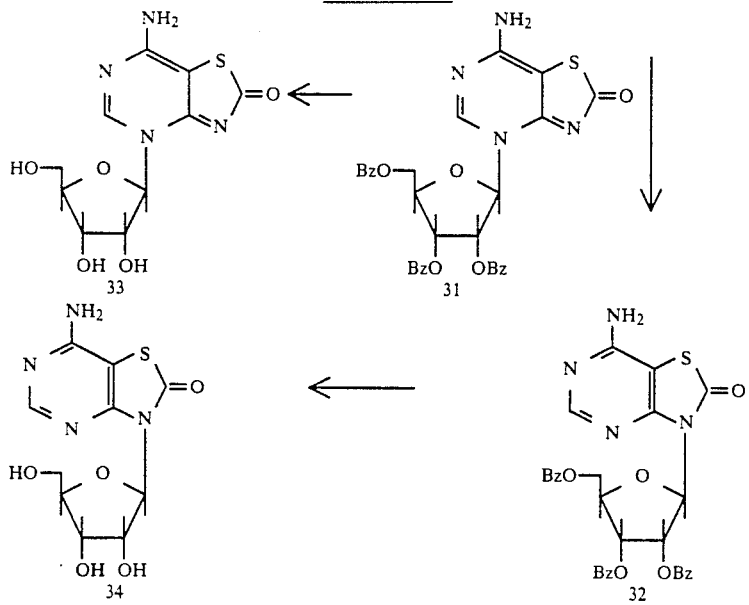

SCHEME VI

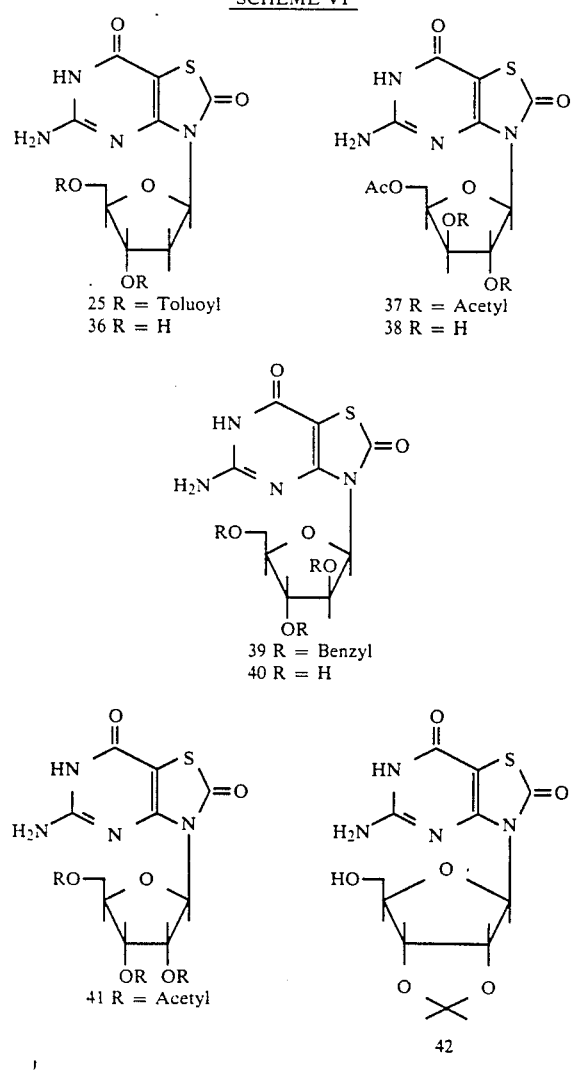

Natural killer cells have been implicated as providing defense against viral infections and malignant cells. Abnormalities in the natural killer cell's activity may thus result in the development of the diseases. Biological immunomodulators may restore or correct certain deficient immune functions. Recently interleukin-2 has been shown to have immunotherapeutic potential in tumor patients. Interleukin-2 and other known immunopotentiators are generally protein in nature and may cause severe side effects upon their administration. Non toxic low molecular synthetic compounds which are not proteins can be suggested for avoiding the side effects of known protein immunotherapeutic potentiators.

EXAMPLE 32

In Vitro Induced Potentiation of Natural Killer Cell Activity

The non protein nucleoside and nucleotide compounds of the invention have shown increased natural killer cell activity. In this example, natural killer cell activity is demonstrated in mice.

Spleen cells from CBA/CaJ or C57BL/6J mice were cultured with 0.05 mM concentrations of compound 7 for 20 to 44 hours at 37° C. in a 5% $CO_2$ humidified atmosphere as described in Djeu, J-Y, Heinbaugh, J. A., Holden, H. T., Herberman R. B.: *Journal Immunology* 122:175, 1979, and Gonzales, H., Karriger, K., Sharma, B., Vaziri, N.: *Federal Procedures* 42:1195, 1983. After incubation the cytotoxicity of the treated and untreated cells was determined against YAC-1 cells. In performing this test both a non-drug control and a control using Poly I:C were run concurrently with compound 7.

TABLE 1

In Vitro Induced Potentiation of Natural Killer Cell Activity[a]

| Effector Cells | | % Natural Killer Cell Cytotoxicity Treatment Time (Hour) | | |
|---|---|---|---|---|
| From: | Treatment With: | 0 | 20 | 44 |
| CBA/CAJ | None | 13 | 4 | 0.5 |
| | Compound 7 | 15 | 34 | 31 |

TABLE 1-continued

*In Vitro* Induced Potentiation of Natural Killer Cell Activity[a]

| Effector Cells | | % Natural Killer Cell Cytotoxicity Treatment Time (Hour) | | |
|---|---|---|---|---|
| From: | Treatment With: | 0 | 20 | 44 |
| | Poly I:C | 14.5 | 18 | 19 |
| CBA/CAJ | None | 14 | 8 | 1 |
| | Compound 7 | 23 | 62 | 44 |
| | Poly I:C | 22 | 31 | 9 |
| C57BL/6J | None | 16 | 1.5 | 2.5 |
| | Compound 7 | 18 | 35 | 34 |
| | Poly I:C | 18 | 13 | 14 |
| C57BL/6J | None | 30 | 1.6 | 1.3 |
| | Compound 7 | 18 | 25 | 22 |
| | Poly I: | 22 | 6 | 13 |

[a]Spleen cells from mice were treated with 0.05 mM concentration of compound 7 in RPMI-1640 medium containing 10% FCS, 0.1 mM nonessential amino acids and $5 \times 10^{-5}$ M Mercaptoethanol. The effector cells were then tested for their cytotoxic activity against YAC-1 target cells in 4 hr $^{51}$Cr release assay.

As is evident from Table 1 incubation for 20 hours with compound 7 augmented natural killer cell cytotoxicity from 4, 8, 1.5 and 1.6% for untreated control to 34, 62, 35 and 25% respectively. Similar treatment for up to 44 hours also caused a distinct increase in natural killer cell activity. Using Poly I:C as a further control, which is a well known potentiator of natural killer cells, compound 7 demonstrated increased activity compared to Poly I:C. The results of Table 1 demonstrate compound 7 markedly induces a high increase in murine natural killer cell activity.

EXAMPLE 33

In Vitro Augmentation of Human Natural Killer Cell Activity

The natural killer cell activity in human cells was also measured. In conducting these tests peripheral blood mononuculear cells (PBMNC) were isolated on Ficoll-Hypaque gradient, washed three times in Hanks and re-suspended in RPMI-1640 containing 10% human AB serum as described in Rosenberg, S. A.: *Journal American Medical Association*, 256:3117, 1986 and the above referred to reference to Djeu, et al. Peripheral blood mononuclear cells (PBMNC) from eleven different donors were treated with compound 7 as described in Djeu, et al. as well as Sharma, B., Odom, L. F.: *Cancer Immunol. Immunother.* 7:93, 1979, and Sharma, B., Odom, L. F.: *Cancer Research* 44:3258, 1984.

The PBMNC cells were incubated with compound 7 at 37° C. for 20 to 68 hours in a 5% $CO_2$ humid atmosphere and after incubation the cytotoxicity was determined against K562 tumor cells. The results are shown in Tables 2a and 2b.

TABLE 2a

*In Vitro* Augmentation of Human Natural Killer Cell Activity[a]

| | % Natural Killer Cell Cytotoxicity | |
|---|---|---|
| Donor | − Compound 7 | + Compound 7 |
| 1 | 26 | 91 |
| 2 | 4 | 29 |
| 3 | 22 | 54 |
| 4 | 24 | 47 |
| 5 | 6 | 16 |
| 6 | 1 | 18 |
| 7 | 2 | 10 |
| 8 | 13 | 22 |
| 9 | 6 | 15 |
| 10 | 14 | 20 |
| 11 | 11 | 32 |

[a]Peripheral blood mononuclear cells were treated with 0.05 − 0.4 mM concentration of compound 7 in RPMI-1640 containing 10% human AB serum for 20 to 68 hours. After the treatment, effector cells were tested against K562 target cells in 4 hour $^{51}$Cr release assay as described in Sharma et al. above. The data shown here represent the maximum response.

TABLE 2b

*In Vitro* Augmentation of Human Natural Killer Cell Activity[a]

| | % Natural Killer Cell Cytotoxicity | | | |
|---|---|---|---|---|
| Exp. # | Donor 1 | | Donor 2 | |
| | −Compound 7 | +Compound 7 | −Compound 7 | +Compound 7 |
| 1 | 25 | 47 | 4 | 29 |
| 2 | 26 | 91 | 15 | 37 |
| 3 | 9 | 36 | 19 | 37 |
| 4 | 23 | 55 | 3 | 26 |
| 5 | 32 | 67 | 4 | 13 |
| 6 | 12 | 30 | 2 | 10 |
| 7 | 16 | 50 | | |
| 8 | 31 | 40 | | |

[a]Peripheral blood mononuclear cells were treated with 0.05 − 0.4 mM concentration of compound 7 in RPMI-1640 containing 10% human AB serum for 20 to 68 hours. After the treatment, effector cells were tested against K562 target cells in 4 hour $^{51}$Cr release assay as previously described above in Sharma et al. The data represent the maximum response.

As evident from Table 2a the PBMNC from eleven donors had a mean natural killer cell cytotoxicity activity of 11.7%. The PBMNC from the same donors which was pretreated with compound 7 expressed a 32.2% mean natural killer cell cytotoxicity. While there is some variability between the eleven donors, eight of the donors showed over 100% potentiation in natural killer cell cytotoxicity. In the other four cases compound 7 treatment in vitro produced a marked increase in natural killer cell mediated cytotoxicity.

As is seen in Table 2b compound 7 also consistently mediated potentiation of human natural killer cells. In the first donor eight individual tests were run and an increase in the mediated potentiation was seen in eight of the eight tests. In the second donor the increase was seen in six of six tests. As is evident from Tables 2a and 2b compound 7 significantly induced higher levels of natural killer cell activity in human cells.

In further reproducibility tests compound 7 was tested for reproducibility in its increase in natural killer cell activity as is shown in Table 2c and further for its reproducibility on human natural killer cell activity as is shown in Table 2d.

TABLE 2c

Reproducibility of Compound 7 Induced Increase in Natural Killer Cell Activity

% Increase in Natural Killer Cell Activity

| | Donor | |
|---|---|---|
| Exp. # | 1 | 3 |
| 1 | 1031 | 220 |

TABLE 2c-continued

Reproducibility of Compound 7 Induced
Increase in Natural Killer Cell Activity

% Increase in Natural Killer Cell Activity

| Exp. # | Donor 1 | Donor 3 |
|---|---|---|
| 2 | 658 | 102 |
| 3 | 413 | 201 |
| 4 | 200 | 66 |
| 5 | 149 | 28 |
| 6 | 460 | 136 |
| 7 | 91 | 102 |
| 8 | 98 | 200 |
| 9 | 200 | |

TABLE 2d

Effect of Compound 7 on Human Natural Killer Cell Activity

| Donor | % Increase in Induced Natural Killer Cell Activity |
|---|---|
| 1 | 1031 |
| 2 | 548 |
| 3 | 220 |
| 4 | 88 |
| 5 | 123 |
| 6 | 141 |
| 7 | 167 |
| 8 | 150 |
| 9 | 0 |
| 10 | 63 |
| 11 | 8 |

EXAMPLE 34

In Vivo Potentiation of Natural Killer Cell Activity in Mice

Compound 7 was further studied for potentiation of natural killer cell activity in vivo in mice. CBA/CaJ mice were treated with compound 7 by injecting 1.68 mg per 0.5 ml per mouse of compound 7. After 1, 2, 3 and 4 days of treatment the spleens of the mice were harvested and the cytotoxic activity of the spleen cells was determined against YAC-1 tumor target cells in the above referred to $^{51}$Cr release assay as identified in EXAMPLE 32. The results of these tests are shown in Tables 3, 4, 5 and 6.

TABLE 3

Natural Killer cell Activity in CBA/CaJ Mice[a]

| Mice CBA/CaJ | Treatment With: | Days After Treatment | % Natural Killer Cytotoxicity Effector: Target 50:1 | 100:1 | 150:1 |
|---|---|---|---|---|---|
| Group - 1 | Saline | 1 | 11 ± 3 | 18 ± 2 | 23 ± 0.3 |
| Group - 2 | Compound 7 (1.68 mg) | 1 | 53 ± 5 | 64 ± 5 | 71 ± 9 |
| Group - 3 | Compound 7 (1.68 mg) | 2 | 46 ± 9 | 64 ± 5 | 65 ± 7 |
| Group - 4 | Compound 7 (1.68 mg) | 3 | 38 ± 6.6 | 50 ± 7 | 63 ± 6 |
| Group - 5 | Compound 7 (1.68 mg) | 4 | 30 ± 0.1 | 37 ± 1.5 | 48 ± 3 |

[a]Three mice in each group were treated with saline or compound 7 (1.68 mg/mouse) by intraperitoneal route. Spleens were removed, cells were isolated and then their cytotoxicity was determined against YAC-1 target cells. Each value represents mean ±SD cytotoxic activity of three mice.

As is evident from table 3 a single injection of compound 7 at 1.68 mg per mouse caused a profound increase in natural killer cell activity. A maximum response of 382% increase was obtained one day after treatment. More than a two fold increase was observed even after 4 days with compound 7.

EXAMPLE 35

Dosage Effects on Natural Killer Cell Activity in Mice

Table 4 shows a dose response treatment with compound 7.

TABLE 4

Dosage Effects on Natural Killer Cell Activity in Mice[a]

| Mice CBA/CaJ | Treatment With: | % Natural Killer Cytoxicity Effector: Target 50:1 | 100:1 | 150:1 |
|---|---|---|---|---|
| Group - 1 | Saline | 14 ± 4 | 20 ± 4 | 23 ± 3.5 |
| Group - 2 | Compound 7 (0.84 mg) | 38 ± 7 | 48 ± 9 | 56 ± 8.5 |
| Group - 3 | Compound 7 (1.68 mg) | 44 ± 8 | 56 ± 12 | 61 ± 14 |
| Group - 4 | Compound 7 (2.52 mg) | 48 ± 6.6 | 62 ± 7 | 70 ± 5 |
| Group - 5 | Compound 7 (3.36 mg) | 48 ± 4.6 | 67 ± 10 | 74 ± 6.4 |

[a]Three mice in each group were treated with saline or compound 7 by i.p. route. Spleens were removed, cells were isolated and then their cytotoxicity was determined against YAC-1 target cells. Each value represents mean ±SD cytotoxic activity of three mice.

As is evident from Table 4 mice were treated with 0.84 mg to 3.36 mg per mouse of compound 7. Although all doses of compound 7 induced a marked increase in natural killer cell activity the maximum augmentation was displayed by mice that received 3.36 mg of compound 7.

EXAMPLE 36

Natural Killer Cell Activity in Old Mice

Twelve week old C57BL/6J mice have been shown (Djeu et al. above) to exhibit little spontaneous natural killer cell activity. Table 5 shows the effect of increase of natural killer cell activity in aging mice (8 Months Old). For this test compound 7 was injected at a dose of 1.67 mg per mouse and 3.34 mg per mouse and after a day the natural killer cell activity of the spleen cells was determined.

TABLE 5

Natural Killer Cell Activity in Old Mice[a]

| Mice C57BL/6J | Treatment With: | % Natural Killer Cell Cytotoxicity Effector: Target 50:1 | 100:1 | 150:1 |
|---|---|---|---|---|
| Group - 1 (8 Mo. Old) | Saline | 4 | 9 | 14 |
| Group - 2 (8 Mo. Old) | Compound 7 (1.67 mg) | 14 | 19 | 23 |
| Group - 3 (8 Mo. Old) | Compound 7 (3.34 mg) | 17 | 28 | 38 |

TABLE 5-continued

Natural Killer Cell Activity in Old Mice[a]

| Mice C57BL/6J | Treatment With: | % Natural Killer Cell Cytotoxicity Effector: Target | | |
|---|---|---|---|---|
| | | 50:1 | 100:1 | 150:1 |
| Group - 4 (8 Wk. Old) | Saline | 5 | 7 | 7 |
| Group - 5 (8 Wk. Old) | Compound 7 (1.67 mg) | 15 | 20 | 24 |
| Group - 6 (8 Wk. Old) | Compound 7 (3.34 mg) | 17 | 27 | 31 |

[a]Three mice in each group were treated with saline or compound 7 by i.p. route. Spleens after treatment were removed, cells were isolated and then their cytotoxicity was determined against YAC-1 target cells. Each value represents mean ±SD cytotoxic activity of three mice.

As is evident compound 7 showed an increase in natural killer cell activity ranging from 4% untreated to 17% treated at a 50:1 effector/target ratio. The magnitude of induction of increase was similar to that displayed by compound 7 in 8 week old mice. This low molecular weight nucleoside compound induced increases in natural killer cell activity which is as high as increases mediated by Poly I:C, LPS, Pyran or interferon as has been reported by Djeu et al above.

EXAMPLE 37

Natural Killer Cell Activity in Nude/Nude Mice

Compound 7 was also able to potentiate markedly the natural killer cell activity in T cell deficient (nude/nude) mice as is shown in Table 6.

TABLE 6

Natural Killer Cell Activity in Nude/Nude Mice[a]

| Mice Nude-Nude | Treatment With: | % Natural Killer Cell Cytotoxicity Effector: Target | | |
|---|---|---|---|---|
| | | 50:1 | 100:1 | 150:1 |
| Group - 1 | Saline | 15 ± 5 | 25 ± 7.7 | 30 ± 11 |
| Group - 2 | Compound 7 (1.67 mg) | 43 ± 12 | 56 ± 12 | 61 ± 14 |
| Group - 3 | Compound 7 (3.34 mg) | 38 ± 6 | 56 ± 6 | 61 ± 12 |

[a]Three mice in each group received saline or compound 7 through i.p. route, spleens were removed one day after the treatment, cells were isolated and then their cytotoxicity was determined against YAC-1 target cells. Each value represents average ±SD cytotoxic activity of three mice.

As is evident from table 6 compound 7 showed an effective increase of over two fold at both doses tested with respect to a saline control.

EXAMPLE 38

In Vivo Potentiation of Cytotoxic Immune Functions Against Tumor

It has been shown in Bear, H. D. *Cancer Research* 6:1805, 1986, that inoculation of tumor cells into mice resulted in tumor growths with concomitant induction of antigen specific T cell mediated immune response. These induced T cells have been shown to inhibit tumor growth in vivo and to cure and/or prolong the life span of tumor bearing mice. Others have further shown that tumor specific T cell mediated immune responses can be potentiated by immunomodulators. This has been shown in the above referred to reference by Bear as well as Herberman, R. B.: *Journal Biol. Resp. Modifiers* 3:527, 1984, Cheever, M. A., Greenbert, P. D., Gillis, S., Fefer, A. In: A. Fefer and A. Goldstein (eds.) pp. 127, New York, Raven Press, 1982, and Rosenberg, S. A., *Journal Biol. Resp. Modifiers* 3:501, 1984.

TABLE 7

In Vivo Potentiation of Cytotoxic Lymphocytes Activity Against Mastocytoma (P815) Tumor Cells Following Injection of Tumor Cells and Drug[a]

| Mice | Inoculation With | Treated With | % Cytotoxicity Days | | | |
|---|---|---|---|---|---|---|
| | | | 3 | 5 | 7 | 9 |
| DBA/2 | P815 | Saline | 13 | 4 | 9 | 9 |
| DBA/2 | P815 | Compound 7 | 30 | 24 | 32 | 27 |
| DBA/2 | P815 | Recombinant Interleukin-2 | 25 | 21 | 25 | 20 |

[a]Ten mice in each group were inoculated with 2 × 10[6] tumor cells. After 5 hours, saline or nucleoside compound 7 solution (2 mg/mouse) was administered to each mouse. On days 3,5,7 or 9, spleen cells were isolated and their cytotoxicity was determined against P815 tumor cells as described in Gonzales and Sharma.

Compound 7 was tested to determine whether or not it can increase cytotoxic lymphocytes response against mastocytoma tumor cells. In the test mice were immunized with mastocytoma cells (P815) and after 5 hours compound 7 as a solution was given in a dose of 2 ml per mouse. Further, recombinant interleukin-2 was utilized as a control given at 50 U per mouse. The ability of spleen cells to kill tumor cells was determined following a single injection of either compound 7 or recombinant interleukin-2.

As Table 7 shows cells from mice treated with compound 7 expressed statistically significant highly cytotoxicity than the control group $p<0.05$. Similarly recombinant interleukin-2 treated mice showed higher cytotoxicity activity as compared to the control group $p<0.05$. The activity of compound 7 and recombinant interleukin-2 was essentially the same showing that compound 7 can potentiate cytotoxic immune responses against tumor cells in vivo.

EXAMPLE 39

In Vitro Potentiation of IgM Production In Human Peripheral Blood Mononuclear Cells (PBMNC)

In this example B cell potentiation is measured by measuring increases of IgM production against Staphylococcus Aureus Cowan (SAC). PBMNC cells were cultured with SAC in the absence and in the presence of compound 7. After 7 and 10 days of incubation supernatants were harvested and assessed for the presence of IgM by ELISA as described in Engvall, E.: *Methods of Enzymology* 70:419, 1980.

TABLE 8

Effect on IgM Production By Human Peripheral Blood Mononuclear Cells *In Vitro*

| Exp. # | Culture | IgM (;g/ml) Day | |
|---|---|---|---|
| | | 7 | 10 |
| 1 | PBMNC alone | 40 | 372 ± 38 |
| | PBMNC + SAC | 1400 ± 282 | 2500 ± 250 |
| | PBMNC + SAC + Compound 7 (0.4 mM) | 7875 ± 883 | 13400 ± 2545 |
| | PBMNC + Compound 7 (0.4 mM) | 1500 ± 424 | 2550 ± 353 |
| 2 | B Cells Alone | 38 | |
| | B Cells + SAC | 1800 | |
| | B Cells + SAC + Compound 7 | 8350 ± 212 | |
| | B Cells + Compound 7 | 1225 ± 176 | |
| 3 | PBMNC alone | 50 | |
| | PBMNC + Compound 7 (0.2 mM) | 1710 ± 127 | |
| | PBMNC + PWM | 560 ± 84 | |

TABLE 8-continued

Effect on IgM Production By Human Peripheral Blood Mononuclear Cells *In Vitro*

| | | IgM (;g/ml) Day | |
|---|---|---|---|
| Exp. # | Culture | 7 | 10 |
| | PBMNC + SAC | 612 ± 53 | |

*PBMNC or enriched B cells from normal donors were cultured alone or with *Staphylococcus Aureus* Cowan (SAC) in the absence and presence of compound 7. After incubation, supernatants were harvested and checked for IgM by ELISA.

As is evident from Table 8 SAC activated PBMNC to produce IgM in both 7 and 10 day cultures. The SAC activated PBMNC cultures which included compound 7, however, displayed a significantly greater level of IgM, over a two fold increase than the cultures without compound 7. Similar increases in IgM production were also observed when enriched B cells were activated with SAC in the presence of compound 7. Compound 7 was able to induce up to 34 fold increases in IgM production. This increase is much higher than the increases induced by the known mitogen 'pokeweed.' The results suggest that compound 7 mediates the potentiation of SAC induced IgM in vitro human culture systems.

EXAMPLE 40

In Vitro Enhancement of Primary Anti-sheep Red Blood Cell Antibody Response

Compound 7 was tested to determine its effects on primary antibody response against sheep red blood cells in vivo. Mice (C57BL/6) in groups of 4 were injected intraperitoneally with 0.1% sheep red blood cell suspended in saline. At various times compound 7 in various concentrations was administered intraperitoneally. The results of this test are shown in Table 9.

TABLE 9

Effect on Primary Anti-Sheep Red Blood Cells Antibody Response*a*

| Mice (C57BL/6) | | SRBC | Compound 7 (mg) | PFC/10$^6$ Spleen Cells |
|---|---|---|---|---|
| I. | Group-1 | + | — | 103 ± 33 |
| | Group-2 | + | 2.97 | 307 ± 156 |
| | Group-3 | + | 4.97 | 371 ± 56 |
| II. | Group-1 | + | — | 81 ± 29 |
| | Group-2 | + | 2.97 | 165 ± 28 |
| | Group-3 | + | 4.95 | 467 ± 170 |
| | Group-4 | + | 4.95 | 433 ± 172 |
| III. | Group-1 | + | — | 44 ± 18 |
| | Group-2 | + | 1.9 | 143 ± 140 |
| | Group-3 | + | 3.3 | 176 ± 105 |

*a*Groups of four C57BL/6 mice were injected i.p. with 6.5 × 10$^6$ SRBC and various doses of compound 7. The number of PFC to SRBC (shown as mean ± SD) were determined on day 6 as described in Cheever.

For Table 9 the number of antibody cells was determined by the modified Jerne, Nordin plaque assay as disclosed in Jerne, N. K., Nordin, A. A., *Science* 140:405, 1963. The results seen in Table 9 show that compound 7 induced a marked increase in the number of antibody forming cells.

Compounds of the invention have also been tested for antiviral activity. Tests have been conducted for both the therapeutic and prophylactic effect of the compounds against a variety of both RNA and DNA viruses.

EXAMPLE 41

Antiviral Activity Against Herpes Simplex Virus Types 1 and 2

In this test Compound 7 was tested against both Herpes Simplex Type 1 Virus and Herpes Simplex Type 2 Virus. The tests were conducted as prophylactic treatments in vivo utilizing the mouse as a model. In each of these tests a placebo was utilized for control purposes. The survival time reflects survival time of those animals which succumbed during the test.

TABLE 10

Antiviral Activity Against Effects of Herpes Simplex Virus Type 1 Infection

| Compound | Dose*a* (mg/kg/day) | Survivors/ Total (%) | Mean Survival Time (days) |
|---|---|---|---|
| Placebo*b* | — | 1/12 (0) | 12.5 ± 3.0 |
| Compound 7 | 200 | 6/12 (50)*c* | 11.0 ± 1.7 |
| Compound 7 | 100 | 4/12 (25) | 11.4 ± 1.8 |
| Compound 7 | 50 | 8/12 (75)*c* | 14.8 ± 5.0 |

*a*Treatments were once a day at −48, −24, and −2 hours relative to virus inoculation.
*b*A 2% sodium bicarbonate solution was used as the placebo and as diluent for Compound 7.
*c*Statistically significant (.025) difference between the drug-treated and placebo control mice, determined by the two-tailed Fisher exact test.

As is shown in Table 10 prophylactic treatment of a Herpes type 1 infection in mice was effectively treated with compound 7. There was some variability in the response with the response at 100 mg per kg dose being less effective than both the lower and higher dosages.

TABLE 11

Antiviral Activity Against Herpes Simplex Virus Type 2 Infection

| Compound | Dose*a* (mg/kg/day) | Survivors/ Total (%) | Mean Survival Time (days) |
|---|---|---|---|
| Placebo*b* | — | 0/12 (8) | 9.8 ± 1.0 |
| Compound 7 | 200 | 2/12 (17) | 7.2 ± 3.9*c* |
| Compound 7 | 100 | 6/12 (50) | 11.2 ± 1.5*d* |
| Compound 7 | 50 | 6/12 (50) | 11.8 ± 2.3*d* |

*a*Treatments were once a day at −48, −24, and −2 hours relative to virus inoculation.
*b*A 2% sodium bicarbonate solution was used as the placebo and as diluent for Compound 7.
*c*Statistically significant (p < .05) difference between the drug-treated and placebo control mice, determined by the two-tailed t-test. Three mice died on days 1 and 2 post-virus inoculation from drug toxicity. The rest of the mice died at 9.6 ± 0.8 days which was about the same as the virus control.
*d*Statistically significant (p < .05) difference between the drug-treated and placebo control mice, determined by the two-tailed t-test.

As is shown in Table 11 prophylactic treatment of a Herpes type 2 infection was effective at all levels tested. At 50 and 100 mg per kg this statistically significance in mean survival time was just outside of the range of a statistical significance of p<0.1 by the two-tailed Fisher exact test. At 200 mg per kg in the mouse the dose was partially toxic.

EXAMPLE 42

Antiviral Activity Against Influenza B Virus Infection in Mice

Compound 7 was tested therapeutically against Influenza B Virus Infection in Mice. In addition to a saline control Ribavirin, a known antiviral, was utilized for test purposes. The results of this test are shown in Table 12.

TABLE 12

Antiviral Activity Against Influenza B Virus Infection in Mice

| Compound | Dose (mg/kg/day) | Treatment Schedule | Survivors/ Total (%) | Mean Survival Time (days) |
|---|---|---|---|---|
| Saline | — | a | 0/12 (0) | 8.7 ± 2.7 |
| Ribavirin | 100 | a | 10/12 (83)[c] | 8.0 ± 0.0 |
| Compound 7 | 100 | b | 2/12 (17) | 6.6 ± 1.1 |
|  | 50 | b | 2/12 (17) | 6.4 ± 1.5 |

[a]Half-daily doses were administered twice a day for 7 days starting 2 hours pre-virus inoculation.
[b]Treated once a day at −2 hours and on days 2, 4, and 6 relative to virus inoculation.
[c]$p < .001$ two-tailed t-test.

As is shown in Table 12 against influenza B in the mouse compound 7 has an efficacy between saline, having no antiviral activity against influenza, and Ribavirin, which has significant antiviral activity against influence.

EXAMPLE 43

Antiviral Activity Against San Angelo Virus Infection in Mice

In this example the antiviral activity against a San Angelo virus, an encephalitis type virus, was measured utilizing both a therapeutic and a prophylactic protocol.

The results of this test are given in Table 13. As with the prior example Ribavirin was utilized as a positive antiviral control and saline as a negative. The results of this test is given in table 13.

As is evident from Table 13 in both a therapeutic and a prophylactic mode compound 7 showed antiviral activity equal to that of Ribavirin against San Angelo encephalitis virus.

EXAMPLE 44

Antiviral Activity Against Mouse Cytomegalovirus Infection in Mice

In this test compound 7 was also tested for both therapeutic or prophylactic efficacy against a mouse cytomegalovirus infection. The results of these tests are shown in Tables 14 and 15.

TABLE 14

Antiviral Activity Against Mouse Cytomegalovirus Infection in Mice

| Compound | Dose (mg/kg/day) | Treatment Schedule | Survivors/ Total (%) | Mean Survival Time (days) |
|---|---|---|---|---|
| Saline | — | a | 4/12 (33) | 6.1 ± 0.4 |
| Compound 7 | 200 | a | 12/12 (100)[c] | >21 |
|  | 100 | b | 7/12 (58) | 7.0 ± 1.4 |
|  | 50 | b | 6/12 (50) | 6.5 ± 0.8 |

[a]Half-daily doses were administered at 24 and 16 hours previrus inoculation
[b]Single dose was administered 24 hours pre-virus inoculation
[c]$p < .005$ two-tailed Fisher exact test

TABLE 15

Antiviral Activity Against Mouse Cytomegalovirus Infection in Mice

| Compound | Dose (mg/kg/day) | Treatment Schedule | Survivors/ Total (%) | Mean Survival Time (days) |
|---|---|---|---|---|
| Saline | — | a | 3/12 (25) | 6.1 ± 0.9 |
| Compound 7 | 100 | b | 0/12 (0) | 6.0 ± 0.8 |
|  | 50 | b | 0/12 (0) | 6.3 ± 1.1 |

[a]Treatments were once a day for 6 days starting 2 hours pre-virus inoculation
[b]Treatments were once a day at −2 hours and on days 2, 4, and 6 relative to virus inoculation As is evident at the 200 mg per kg dose compound 7 exhibited a 100% cure when tested in a prophylactic mode. However, as is seen in Table 15 this activity was not repeated in a therapeutic mode.

TABLE 13

Antiviral Activity Against San Angelo Virus Infection in Mice

| Compound | Dose (mg/kg/day) | Treatment Schedule | Survivors/ Total (%) | Mean Survival Time (21 days) |
|---|---|---|---|---|
| Saline | — | a | 2/12 (17) | 7.5 ± 1.2 |
| Ribavirin | 200 | a | 11/12 (92)[e] | 12.3 ± 2.9 |
| Compound 7 | 200 | b | 12/12 (100)[e] | >21 |
|  | 100 | c | 12/12 (100)[e] | >21 |
|  | 50 | c | 12/12 (100)[e] | >13.0 ± 0.0 |
| Compound 7 | 200 | d | 12/12 (100)[e] | >21 |

[a]Half-daily doses were administered twice a day for 7 days starting 2 hours pre-virus inoculation.
[b]Treated once a day at −2 hours and on days 2, 4, and 6 relative to virus inoculation. Half daily doses were administered twice a day.
[c]Treated once a day at −2 hours and on days 2, 4, and 6 relative to virus inoculation.
[d]Half-daily doses were administered at 24 and 16 hours pre-virus inoculation.
[e]$p < .02$ two-tailed Fisher exact.

EXAMPLE 45

Antiviral Activity Against Semliki Forest Virus Infection in Mice

Antiviral activity was also tested against Semliki Forest Virus an Encephalitis type virus. In this example compounds 7 and 36 were tested for therapeutic efficacy and additionally compound 7 was tested for prophylactic efficacy. Results of this test are shown in Table 16 for the therapeutic mode and in Table 17 for the prophylactic mode.

TABLE 16

Therapeutic Antiviral Activity Against Semliki Forest Virus Infection in Mice

| Compound | Dose (mg/kg/day) | Treatment Schedule | Survivors/ Total (%) | Mean Survival Time (days) |
|---|---|---|---|---|
| Saline | — | a | 0/12 (0) | 6.7 ± 1.9 |
| Compound 7 | 200 | b | 7/12 (58)$^e$ | 4.2 ± 0.8 |
|  | 100 | c | 8/12 (67)$^e$ | 7.3 ± 0.5 |
|  | 50 | c | 4/12 (33) | 6.6 ± 0.8 |
| Compound *36 | 200 |  | 10/12 (83)$^f$ | 7.0 ± 0.0 |
|  | 100 |  | 6/12 (50) | 6.8 ± 0.8 |
|  | 50 |  | 4/12 (33) | 6.1 ± 1.1 |

$^a$Half-daily doses were administered twice a day for 7 days starting 2 hours pre-virus inoculation
$^b$Treated at −2 hours and on days 2, 4, and 6 relative to virus inoculation. Half-daily doses were administered twice a day because of insolubility
$^c$Treated once a day at −2 hours and on days 2, 4, and 6 relative to virus inoculation
$^d$Half-daily doses were administered at 24 and 16 hours pre-virus inoculation
$^e$p < .01 two-tailed Fisher
$^f$p < .02 two-tailed Fisher

TABLE 17

Prophylactic Antiviral Activity Against Semliki Forest Virus Infection in Mice

| Compound | Dose (mg/kg/day) | Treatment Schedule | Survivors/ Total (%) | Mean Survival Time (days) |
|---|---|---|---|---|
| Saline | — | d | 1/8 (12) | 10.4 ± 1.3 |
| Compound 7 | 200 | d | 4/8 (50) | 11.8 ± 2.9 |

$^a$Half-daily doses were administered twice a day for 7 days starting 2 hours pre-virus inoculation
$^b$Treated at −2 hours and on days 2, 4, and 6 relative to virus inoculation. Half-daily doses were administered twice a day because of insolubility
$^c$Treated once a day at −2 hours and on days 2, 4, and 6 relative to virus inoculation
$^d$Half-daily doses were administered at 24 and 16 hours pre-virus inoculation
$^e$p < .01 two-tailed Fisher As is evident from Tables 16 and 17 compound 7 exhibited antiviral activity in both a therapeutic mode and a prophylactic mode against this virus. Further compound 36 also exhibited therapeutic antiviral activity against this virus.

As is evident from the above tables antiviral activity against a variety of viruses is seen. In a further test little or no antiviral activity for compound 7 was demonstrated against influenza B virus and Friend Leukemia virus induced splenomegaly.

EXAMPLE 46

Antiviral Activity Against Human Coronavirus

In this experiment, 14 day old mice were inoculated intracerebrally with human coronavirus. They were treated with compound 7 in a divided intraperitoneal dose at −24 and −18 hours relative to virus inoculation. As shown in the following Table 18, a statistically significant benefit against this viral infection in the brain was provided to the mice at 200 and 100 mg/kg.

TABLE 18

Antiviral Activity Against Human Coronavirus Infection In 14 Day Old Mice

| Test Compound$^a$ (mg/kg) | Survivors/ Total (%) | Mean Survival Time$^b$ (Days) |
|---|---|---|
| 0$^c$ | 0/33 (0) | 6.0 ± 1.6$^d$ |
| 200 | 4/32 (13) | 7.0 ± 1.4$^e$ |
| 100 | 8/33 (24)$^f$ | 7.2 ± 2.0$^e$ |
| 50 | 0/33 (0) | 6.9 ± 2.2 |

$^a$Half daily doses were administered at −24 and −18 hours relative to virus inoculation.
$^b$Of mice that died. Survivors lived through 21 days.
$^c$A 2% sodium bicarbonate solution served as the placebo and as diluent for the test Compound.
$^d$Standard Deviation.
$^e$Statistically significant (p < .01), determined by a two-tailed t-test.
$^f$Statistically significant (p < .01), determined by the two-tailed Fisher exact test.

As is evident from table 18 compound 7 shows antiviral activity against this human virus which was inoculated into the brain.

EXAMPLE 47

Antiviral Activity Against Rat Coronavirus

Four to five day old suckling rats were infected intranasally with rat coronavirus. One day previously a divided intraperitoneal dose of compound 7 or placebo was given. As shown in the following Table 19, a high percentage of the rats treated with compound 7 survived this lung infection. Further the rats that died lived longer than the placebo-treated controls.

TABLE 19

Antiviral Activity Against Rat Coronavirus Infection In Suckling Rats

| Test Compound (μM)$^a$ | Survivors/ Total (%) | Mean Survival Time$^b$ (Days) |
|---|---|---|
| 0$^c$ | 7/28 (25) | 7.2 ± 1.8$^d$ |
| 200 | 22/27 (81)$^e$ | 13.0 ± 1.0$^f$ |

TABLE 19-continued

| Antiviral Activity Against Rat Coronavirus Infection In Suckling Rats | | |
|---|---|---|
| Test Compound ($\mu$M)[a] | Survivors/ Total (%) | Mean Survival Time[b] (Days) |
| 100 | 17/28 (61)[e] | 10.2 ± 1.8[f] |
| 50 | 21/28 (75)[e] | 10.1 ± 2.3[f] |

[a]Half daily doses were administered at −24 and −18 hours relative to virus inoculation.
[b]Of rats that died. Survivors lived through 21 days.
[c]A 2% sodium bicarbonate solution served as the placebo and as diluent for the test compound.
[d]Standard Deviation.
[e]Statistically significant (p < .02), determined by a two-tailed Fisher exact test.
[f]Statistically significant (p < .002), determined by the two-tailed t-test.

EXAMPLE 48

Antiviral Activity Against Encephalomyocarditis Viral Infection In Mice

In this experiment, the effects of different treatment regimens of compound 7 on the outcome of an Encephalomyocarditis viral infection in mice was studied. Treatments were started 24 hours pre-virus. A single dose of 200 mg/kg was given to two groups of mice. One of the groups then received single injections of compound 7 at 50 mg/kg for 6 more days. Results were compared to a placebo control treated as was the 50 mg/kg group. As shown in the following Table 20 there is clear evidence that mice receiving the daily dose of 50 mg/kg were protected to a greater degree than the mice which only got the single 200 mg/kg dose. The former group had less mortality and extended means survival times.

TABLE 20

| | Effects of single versus multiple treatments on Encephalomyocarditis virus infection in mice | | | |
|---|---|---|---|---|
| Compound | Treatment[a] −24 hrs | Treatment[a] Day 0-6 | Survivors/ Total (%) | Mean Survival Time[b] (Days) |
| Placebo[c] | + | + | 1/12 (8) | 4.4 ± 0.5[d] |
| Test Compound | 200 | — | 5/12 (42) | 6.0 ± 1.3[e] |
| Test Compound | 200 | 50 | 8/12 (67)[f] | 9.5 ± 2.1[e] |

[a]Single injections were given at the times indicated. The numbers in the columns refer to the dose of the test compound in mg/kg or mg/kg/day.
[b]Of mice that died. Survivors lived through 21 days.
[c]A 2% sodium bicarbonate solution served as the placebo and as diluent for the test compound.
[d]Standard Deviation.
[e]Statistically significant (p < .002), determined by a two-tailed t-test.
[f]Statistically significant (p < .02), determined by the two-tailed Fisher exact test.

EXAMPLE 49

Antiviral Activity of Nucleosides and Nucleotides on Murine Natural Killer Cell Activity In Vitro Other compounds of the invention were tested with respect to their natural killer cell activity utilizing mouse spleen cells as per example 32 above. The results of these tests are tabulated in Table 21.

TABLE 21

| Effect of Guanosine Nucleosides and Nucleotides on Murine Natural Killer Cell Activity In Vitro[a] | | | |
|---|---|---|---|
| Exp # | Effector Cells Pretreated with: | Concentration (mM) | % Natural Killer Cell Cytotoxicity |
| 1 | None | — | 1.2 |
| | Compound 7 | 0.05 | 34.5 |
| | Compound 16 | 0.05 | 10 |
| | Compound 16 | 0.5 | 38 |
| | Compound 9 | 0.05 | 3 |
| | Compound 9 | 0.5 | 13 |
| 2 | None | — | 1.6 |
| | Compound 7 | 0.05 | 25 |
| | Compound 7 | 0.25 | 28 |
| | Compound 16 | 0.05 | 3 |
| | Compound 16 | 0.25 | 17 |
| | Compound 9 | 0.05 | 2 |
| 3 | None | — | 1.6 |
| | Compound 7 | 0.05 | 28 |
| | Compound 16 | 0.05 | 14 |
| | Compound 16 | 0.25 | 24 |
| | Compound 9 | 0.05 | 0.31 |
| | Compound 9 | 0.5 | 6.5 |

[a]Spleen cells from mice were incubated in the absence and presence of various compounds. After incubation, cells were suspended in complete medium and then their cytotoxic activity was determined against YAC-1 target cells as described in the text

EXAMPLE 50

Effect of Nucleosides and Nucleotides on Human Natural Killer Cell Activity In Vitro Other Nucleosides and Nucleotides of the invention were tested for their activity in human natural killer cells in vivo as per example 33 above. The results are tabulated in Table 22.

TABLE 22

| Effect of Guanosine Nucleosides and Nucleotides on Human Natural Killer Cell Activity In Vitro | | | |
|---|---|---|---|
| Exp # | Effector Cells Pretreated with: | Concentration (mM) | % Natural Killer Cell Cytotoxicity |
| 1 | None | — | 26 |
| | Compound 7 | 0.4 | 91 |
| | Compound 16 | 0.4 | 69 |
| | Compound 12 | 0.4 | 39 |
| | Compound 11 | 0.4 | 63 |
| 2 | None | — | 23 |
| | Compound 12 | 0.2 | 43 |
| 3 | None | — | 17 |
| | Compound 12 | 0.4 | 22 |
| 4 | None | — | 9 |
| | Compound 11 | 0.4 | 19 |
| 5 | None | — | 3 |
| | Compound 7 | 0.4 | 37 |
| | Compound 16 | 0.4 | 10 |
| | Compound 9 | 0.05 | 6 |
| 6 | None | — | 16.53 |
| | Compound 7 | 0.4 | 50 |
| | None | — | 40 |
| | Compound 9 | 0.2 | 43 |
| 7 | None | — | 4.5 |
| | Compound 7 | 0.2 | 10 |
| | Compound 8 | 0.2 | 5 |
| | Compound 19 | 0.2 | 7 |

EXAMPLE 51

Tumoricidal Activity of Macrophages In Mice

The activity of compound 7 with respect to its ability to activate macrophages was tested by injecting CBA/CaJ mice with a single dose of compound 7 (2 mg per mouse) and after 24 hours the cytotoxicity of the spleen cells (SC), non adherent SC and adherent SC was determined. The results are shown in Table 23.

TABLE 23

Activation of Macrophages following
Single Injection of Compound 7 in Mice[a]

| Effector Cells | Dose (mg) of Compound 7/mouse | % Cytotoxicity Assay | |
|---|---|---|---|
| | | 4 hrs. | 20 hrs. |
| Spleen Cells (SC) | None | 15 | 41 |
| Nonadherent (SC) | 2 | 45 | 70 |
| Adherent cells | 2 | 37 | 69 |

[a] A group of four mice (CBA/CaJ) were injected with 2 mg/mouse of compound 7 solution. Control group received saline. After 24 hours of injection, spleens were harvested. Adherent and nonadherent cells were separated by incubation of spleen cells on plastic plates for one hour. Cell suspension of spleen cells, nonadherent cells (NC) and adherent cells (AC) were prepared in complete medium. Cytotoxicity of SC, NC and AC was then measured against P8/5 tumor target cells in 4 hrs and 20 hrs chromium release assay.

As is evident from Table 23 compound 7 was able to activate both natural killer and adherent (macrophage) cells as evidenced by the ability of these cells to exert augmented cytotoxicity against tumor target cells.

In examples 52 and 53 the combination activity of compounds of the invention with the known antiviral agent Ribavirin against San Angelo Virus and Banzi Virus were measured utilizing compound 7 in a prophylactic protocol. The Ribavirin served as a further antiviral agent for use in combination with the compounds of the invention.

EXAMPLE 52

Combination Chemotherapy Against San Angelo Virus In Mice

The combination chemotherapy results against San Angelo Virus in Mice are shown in Table 24.

TABLE 24

Combination Chemotherapy Against San Angelo Virus

| Treatment[a] | | Survivors/ | Mean Survival |
|---|---|---|---|
| −24 Hrs | Days 0-6 | Total (%) | Time[b] (Days) |
| Saline | Saline | 1/16 (6) | 8.3 ± 1.8[c] |
| Compound 7 (5)[d] | Saline | 7/16 (44)[e] | 9.6 ± 1.6 |
| Saline | Ribavirin (50) | 6/16 (38) | 9.0 ± 1.2 |
| Saline | Ribavirin (25) | 9/16 (56)[e] | 8.1 ± 0.7 |
| Compound 7 (5) | Ribavirin (50) | 8/16 (50)[e] | 8.9 ± 2.2 |
| Compound 7 (5) | Ribavirin (25) | 6/16 (38) | 10.1 ± 3.6 |

[a] A single injection of saline or compound 7 was given 24 hours before virus inoculation. Treatments on days 0-6 were twice a day for 7 days starting 2 hours pre-virus inoculation.
[b] Of mice that died.
[c] Standard Deviation.
[d] The dose in mg/kg/day is in parentheses.
[e] Statistically significant (p < .05), determined by the two-tailed Fisher exact test.

EXAMPLE 53

Combination Chemotherapy Against Banzi Virus Infection In Mice

The combination chemotherapy results against Banzi Virus infection in mice are shown in Table 25.

TABLE 25

Combination Chemotherapy Against Banzi Virus Infection

| Treatment[a] | Treatment[b] | Survivors/ | Mean Survival |
|---|---|---|---|
| −24 hours | days 0-6 | Total (%) | Time[c] (days) |
| Placebo[d] | Saline | 0/12 (0) | 7.7 ± 0.5 |
| Placebo | Ribavirin 100 mg/kg | 0/12 (0) | 8.5 ± 1.0[e] |
| Placebo | Ribavirin 200 mg/kg | 0/12 (0) | 9.1 ± 0.8[e] |
| Compound 7 100 mg/kg | Saline | 0/12 (0) | 9.3 ± 1.0[e] |
| Compound 7 100 mg/kg | Ribavirin 100 mg/kg | 0/12 (0) | 10.2 ± 0.9[e] |
| Compound 7 | Ribavirin | 3/12 (25) | 12.4 ± 3.5[e] |

[a] Single injection given 24 hours before virus inoculation.
[b] Half-daily doses given twice a day for 7 days starting 2 hours pre-virus inoculation.
[c] Of mice that died. Survivors lived 21 days.
[d] A 2% sodium bicarbonate solution was the placebo and diluent for compound 7. Ribavirin was dissolved in saline.
[e] Statistically significant (p < .05), determined by a two-tailed t-test.

As is evident from Tables 24 and 25, compound 7 in a prophylactic mode in combination with the known antiviral Ribavirin, exhibited efficacy against the test viruses.

Compounds of the invention have further shown the ability to suppress metastasis in host mammals bearing metastatic tumors and in artificially induced metastatsis in such hosts.

Utilizing the protocol of Alessandri, G., Giavazzi, R., Falautano, P., Spreafico, F., Garattini, S., and Mantovani, A., European J. Cancer, 17:651-658, 1981, the antimetastatic activity of Compound 7 is seen in a sarcoma M5076 tumor system.

EXAMPLE 54

Reduction of Reticulum-cell Sarcoma Metastatic Foci

Fragments of reticulum-cell sarcoma M5076 were introduced into mice. The animals were treated with compound 7 for 20 days at various dosages. After treatment, the required tissues were collected, fixed in Bouin's solution and subjected to microscopic observation to enumerate metastatic foci. The results are shown in table 26 as the number of metastatic foci and table 27 as the number of mice with metastatic foci. In table 26 both the range and the median number of foci for each test group is indicated.

TABLE 26

Metastatic Foci Formed In Lungs And Liver
In Response to Reticulum-cell Sarcoma M5076[a]

| Drug[c] | Number of Metastatic Foci In | | | |
|---|---|---|---|---|
| | Lung | | Liver | |
| (mg/kg) | Median | Range | Medium | Range |
| 0 | 18 | (6-30) | 154 | (61-275) |
| 37 | 6 (p < 0.01)[b] | (1-11) | 1 (p < 0.005)[b] | (0-17) |
| 62 | 2 (p < 0.09)[b] | (0-29) | 0 (p < 0.005)[b] | (0-1) |
| 104 | 0 (p < 0.003)[b] | (0-4) | 0 (p < 0.0009)[b] | (0-0) |

[a] Fragments of reticulum-cell sarcoma M5076 (≈ 14 mg) were implanted sc in the left flank of BDF₁ female mice and ip bolus injections of drug were initiated 24 hrs later. The drug was delivered on the basis of 0.01 ml/g mouse weight. Control mice received a 0.09% solution of NaCl delivered on the same basis. Seven mice were used per treatment group. Treatment give qd for days 1-20.
[b] Student t-test.
[c] Compound 7

TABLE 27

Number of Mice having Metastatic Foci Formed In Lungs And Liver In Response to Reticulum-cell Sarcoma M5076[a]

| Drug[c] (mg/kg) | Mice With Metastatic Foci In | |
|---|---|---|
| | Lung (+/7) | Liver (+/7) |
| 0 | 7/7 | 7/7 |
| 37 | 7/7 | 4/7 ($p < 0.05$)[b] |
| 62 | 6/7 | 1/7 ($p < 0.005$)[b] |
| 104 | 3/7 ($p < 0.025$)[b] | 0/7 ($p < 0.0005$)[b] |

[a]Fragments of reticulum-cell sarcoma M5076 ($\approx$ 14 mg) were implanted sc in the left flank of BDF$_1$ female mice and ip bolus injections of drug were initiated 24 hrs later. The drug was delivered on the basis of 0.01 ml/g mouse weight. Control mice received a 0.09% solution of NaCl delivered on the same basis. Seven mice were used per treatment group. Treatment given qd for days 1-20.
[b]Chi-square analysis.
[c]Compound 7

As is evident from tables 26 and 27 there was a statistically significant reduction in the number of metastatic foci in both the lung and the liver. Further the test drug exhibited a dose response with a total suppression of liver metastatic foci seen in some of the test animals at all test doses and a suppression of lung metastatic foci seen at doses greater than 62 mg/kg.

EXAMPLE 55

Increase in Mean Life Span Against Metastatic Reticulum-cell Sarcoma M5076

Effect of drug treatment on the mean life span of host animals implanted with metastatic reticulum-cell sarcoma M5076 was measured using the same test protocol as per example 54. The host animals were drug dosed for 20 days as per example 54, however, as opposed to example 54 they were monitored for survival. The results of these test are shown in table 28.

TABLE 28

Effect Of Drug treatment On The Mean Life Span Of Mice In Response To Metastatic Reticulum-cell Sarcoma M5076[a]

| Drug[c] (mg/kg) | Postinoculation Life Span (days) | Increased Life Span (% of Control) |
|---|---|---|
| 0 | 30.33 ± 3.88 | — |
| 37 | 32.33 ± 3.67 | 7.0 |
| 62 | 36.33 ± 0.82 (p 0.01)[b] | 19.8 |
| 104 | 36.50 ± 4.55 ($p < 0.03$)[b] | 20.3 |

[a]Fragments of reticulum-cell sarcoma M5076 ($\approx$ 14 mg) were implanted sc in the left flank of BDF$_1$ female mice and ip bolus injections of drug were initiated 24 hrs later. The drug was delivered on the basis of 0.01 ml/g mouse weight. Control mice received a 0.09% solution of NaCl delivered on the same basis. Six mice were used per treatment group. Treatment give qd for days 1-20 and animals monitored after treatment for survival.
[b]Student t-test.
[c]Compound 7

As is evident from table 28 there was a statistically significant increase in the life span of the host animals seen at the 62 mg/kg or greater dose level.

EXAMPLE 56

Effect of Treatment Against Artificially Induced Metastatic Foci of B16 Melanoma Artificially induced metastatic foci of murine B16 melanoma were induced in mice utilizing the procedure of Mazumder, A., and Rosenberg, S. A., *J. Experimental Medicine*, 154:495, 1984. Test drug, compound 7, was given to groups of test animals. The groups includes a first control group, a second group given drug 24 hours prior to intravenous tumor injection, a third group given drug both 24 hours prior to intravenously tumor injection and 72 hours post tumor injection and a fourth group given drug 72 hours post tumor injection. The mean number of induced pulmonary metastatic foci were determined as shown in table 29.

TABLE 29

Reduction Of The Number of Artificially Induced Pulmonary Metastatic Foci Of Murine B16 Melanoma[a]

| Test Group | Treatment (Hrs) | | | Mean No. Of Metastatic Foci in Lungs |
|---|---|---|---|---|
| | −24 | 0 | 72 | |
| Control | | B16 | | 34 |
| Group 2 | Compound 7 | | | 8 |
| Group 3 | Compound 7 | B16 | Compound 7 | 3 |
| Group 4 | | B16 | Compound 7 | 14 |

[a]10 week old, female C57B1/6 mice in groups of 5 each were injected intravenously with 5 × 10$^5$ of B16 melanoma tumor cells. The mice in groups 2, 3 and 4 were treated by injection of 100 mg/kg of drug intraperitoneally.

As is evident in table 29, in all instances the drug treated groups exhibited a lower mean number of metastatic foci compared to the control. There was at least a 50% reduction in the number of metastatic foci between the control group and each of the drug treated groups and an even greater significant difference noted between the control and the group treated both prior to and post injection of the tumor cells.

Further antitumor effects have been demonstrated against P388 tumors utilizing standard National Cancer Institute tumor test protocol. In the following two examples utilizing this test tumor system increases in the means life span of P388 inoculated mice and the number of animals responsive to different tumor inoculum concentrations, varying drug concentrations and schedules are shown.

EXAMPLE 57

Effect Of Drug Delivery Regiments On Mean Life Span Of P388 Inoculated Mice

In this example as summarized in table 30, different drug delivery regimen were utilized for compound 7 against P388 in the mouse and the postinoculation life span, the change in life span and the number of viable tumor cells at day 6 measured. For this test the data shown are pooled by schedule without regard for dosage. Each treatment group included a total of 15 mice divided into sub-groups of 5 mice treated respectively with 37, 62 or 104 mg/kg/injection of drug per subgroup. After treatment the test animals were monitored for survival.

TABLE 30

Effect Of Treatment On The Mean Life Span Of P388 Inoculated Mice[a]

| Days of Drug[c] Delivery | Postinoculation Life Span (days) | Change in Life Span (% of Control) | Viable Cells Day 6 (% of Control) |
|---|---|---|---|
| Control | 8.18 ± 0.87 | — | — |
| qd, day 2 | 8.60 ± 0.51 p 0.12[b] | 5 | 73 |
| qd, day 2,4 | 8.73 ± 0.59 $p < 0.12$[b] | 7 | 66 |
| qd, day 2-6 | 9.13 ± 0.52 $p < 0.001$[b] | 12 | 49 |

[a]P388 ascites cells (1 × 10$^6$) were implanted ip in BDF$_1$ female mice on day 0, and ip bolus injections of drug were delivered once daily on the days indicated. The drug was delivered on the basis of 0.01 ml/g mouse weight. Control mice received a 0.09% solution of NaCl delivered on the same basis.
[b]Student t-test.
[c]compound 7

EXAMPLE 58

Variation in P388 Test Inoculum, Drug Inoculum And Schedule Of Drug Administration For this example varying concentrations of the number of test cells utilized for P388 inoculum and concentrations of compound 7 were utilized with various schedules of drug administration. For these tests optimization of variables was not attempted and because of this and the number of variables in this test, the results shown in table 31 are interpreted qualitatively with 26 of the 34 groups (76%) showing an increase in life span compared to the remaining 8 groups which showed no increase in life span.

TABLE 31

Response of P388 Inoculated Mice to Various Drug Dosages, Inoculated Concentrations and Dosage Schedules[a]

| Study No. | P388 Cell Conc. | No. of Mice | Dosage mg/kg/inj | Schedule of Admin. | % Increased Life Span |
|---|---|---|---|---|---|
| 1 | $1 \times 10^2$ | 3 | 104 | day 1 | 0 |
|   |   | 3 | 62 | day 1 | (1 cure) |
|   |   | 3 | 37 | day 1 | (2 cures) |
|   |   | 3 | 104 | day 1–9 | 10 |
|   |   | 3 | 62 | day 1–9 | 33 |
|   |   | 3 | 37 | day 1–9 | 0 |
| 2 | $1 \times 10^2$ | 5 | 37 | day 1 | 3 |
|   |   | 5 | 22 | day 1 | 7 |
|   |   | 5 | 13 | day 1 | 7 |
|   |   | 5 | 8 | day 1 | 9 |
| 3 | $1 \times 10^4$ | 3 | 104 | day 1 | 0 |
|   |   | 3 | 62 | day 1 | 0 |
|   |   | 3 | 37 | day 1 | 2 |
|   |   | 3 | 104 | day 1–9 | 6 |
|   |   | 3 | 62 | day 1–9 | 2 |
|   |   | 3 | 37 | day 1–9 | 0 |
| 4 | $1 \times 10^6$ | 3 | 104 | day 1 | 9 |
|   |   | 3 | 62 | day 1 | 0 |
|   |   | 3 | 37 | day 1 | 0 |
|   |   | 3 | 104 | day 1–9 | 23 |
|   |   | 3 | 62 | day 1–9 | 5 |
|   |   | 3 | 37 | day 1–9 | 5 |
| 5 | $1 \times 10^6$ | 5 | 104 | day 2 | 10 |
|   |   | 5 | 62 | day 2 | 5 |
|   |   | 5 | 37 | day 2 | 0 |
|   |   | 5 | 104 | day 2,4 | 5 |
|   |   | 5 | 62 | day 2,4 | 8 |
|   |   | 5 | 37 | day 2,4 | 8 |
|   |   | 5 | 104 | day 2–6 | 12 |
|   |   | 5 | 62 | day 2–6 | 15 |
|   |   | 5 | 37 | day 2–6 | 8 |
| 6 | $1 \times 10^6$ | 7 | 140 | day 2 | 4 |
|   |   | 7 | 140 | day 2,6 | 20 |
|   |   | 7 | 140 | day 2,4,6,8 | 21/1[b] |

[a]P388 ascites cells were implanted ip in the concentrations indicated in BDF$_1$ female mice on day 0, and ip bolus injections of drug were delivered once daily on the days indicated in the conentrations indicated. Control mice received a 0.09% solution of NaCl delivered on the same basis.
[b]toxic in one animal

EXAMPLE 59

Effects Of Drug Treatment On The Mean Life Span Of C26 Inoculated Mice

In a manner similar to the P388 treatment noted above, compounds of the invention were also tested as to their effect against C26 inoculated tumor in mice. The results of this test are shown in table 32. For use with this tumor National Cancer Institute protocol was used.

TABLE 32

Effects of Treatment On Mean Life Span of C26 Inoculated Mice[a]

| Compound 7 mg/kg | Postinoculation Life Span (days) | Last Death on day | Increased Life Span (% of Control) |
|---|---|---|---|
| 0 | 18.30 ± 2.58 | 23 | — |
| 37 | 23.90 ± 10.29 | 41 (53[b]) | 30.6 |
| 62 | 19.80 ± 2.94 | 27 | 8.2 |
| 104 | 20.22 ± 8.53 | 20 (53[b]) | 10.5 |

[a]CDF$_1$ female mice were inoculated ip on day 0 with colon carcinoma C26 (0.5 ml of a 1:100 tumor brei formed by mincing tumor fragments in TC199) and ip bolus injections of drug were initiated 24 hours later. The drug was delivered on the basis of 0.01 ml/g mouse weight. Control mice received a 0.09% solution of NaCl delivered on the same basis. There were 10 mice/treatment group. After treatment qd days 1–20, the mice were monitored for survival.
[b]Certain treated mice lived twice as long as the last control mice and on day 53 test was terminated with mice still alive. One mouse treated with 104 mg/kg of drug did not have any grossly detectable tumor on termination day.

While we do not wish to be bound by theory, it is believed that the antitumor activity of the compounds of the inventions are not as a result of their chemical cytotoxic effect but are the result of drug stimulation of the host animal immune system to kill the tumor cells. This mechanism is implicated from table 30, which shows while only a modest increase in life span was noted for the test period upwards of 51% of the tumor cells were killed and from table 31 which indicates that at various drug concentrations, tumor cell inoculate concentrations and dosage schedules, over 75% of the test protocols resulted in a positive increase in life span with certain of the protocols resulting in cures. As is shown in table 32 increases in life span are also seen in other tumor systems.

The compounds of the invention can be given to a warm blooded host in need thereof in appropriate formulations wherein the compounds comprise the active ingredient of the formulations. Thus the compounds of the invention can be made up into injectables suitable for intravenous or other type injection into the host animal. Further they can be given in an appropriate oral formulation as for instance as an oral syrup preparation, an oral capsule or oral tablet. An additional route of administration might be as a suppository.

For an injectable the compounds would be dissolved in a suitable solution as for instance in a sodium bicarbonate or other buffer. Such a solution would be filtered and added to appropriate ampoules or vials and sealed and sterilized.

As a syrup, the compounds in buffered solution would be mixed with an appropriate syrup with mild stirring. For capsules the dry compounds would be blended with appropriate fillers, binders or the like as for instance Lactose USP powder or Sterotex powder. For the preparation of tablets the compounds of the invention would be mixed with suitable binders and fillers as for instance corn starch NF, Microcrystalline Cellulose, Sterotex powder and water and dried to a low water content. This would be followed by screening, milling, further screening and pressing into the appropriate tablets.

For suppositories, the compounds would be dissolved into appropriate melts of Polyethylene Glycol as for instance Polyethylene Glycol 1540 and 8000 at 60° and formed into the suppositories by molding at 25°.

In addition to the above formulations, the compounds of the invention could also be administered utilizing other delivery technique such as incorporating the compounds of the invention with liposomes and the like.

Additionally, prodrug forms of the compounds of the invention could be utilized to facilitate dispensing, uptake, absorption, metabolic control and the like. One such prodrug is compound 41, the tri-acetate ester of compound 7. Further prodrugs might allow for enzymatic conversion in vivo of analogs of the compounds of the invention into compounds of the invention.

For the purpose of brevity in certain chemical figures and schemes of this specification and the claims attached hereto, different tautomeric forms of the heterocycles of certain compounds have been shown between the various figures and schemes. It is understood that regardless of whether or not substituents are shown in their enol or their keto form, they represent the same compound. Thus, in the claims, the abstract and the brief description in order to utilize only a single structural figure, oxygen and sulfur substituents in the 5 and 7 ring positions are shown in an enolate form whereas in the various schemes these substituents are shown in their normal keto form.

SCHEME V
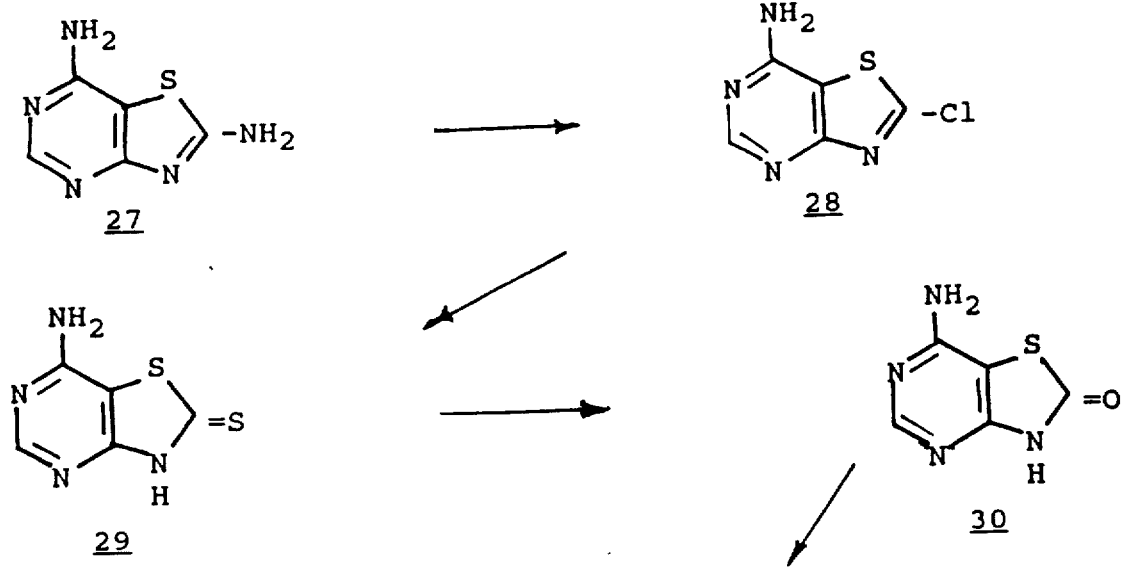

What is claimed is:

1. A method of enhancing an immune response of a mammalian host consisting essentially of:
   administering to said mammalian host a therapeutically effective amount of a compound of the structure:

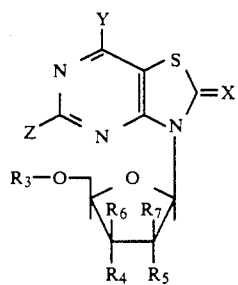

wherein $R_4$, $R_5$, $R_6$ and $R_7$ individually are H, OH or $C_1$-$C_{18}$ O-acyl and $R_3$ is H, $C_1$-$C_{18}$ acyl or

or $R_5$ and $R_7$ are H or OH, $R_6$ is H and together $R_3$ and $R_4$ are

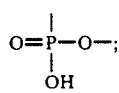

and X is $=$O or $=$S; Y is —OH, —SH, —NH$_2$ or halogen; and Z is H, —NH$_2$, —OH or halogen; wherein halogen is Cl or Br; or a pharmaceutically acceptable salt thereof.

2. A method of claim 1 wherein:
   said compound is a compound of the structure:

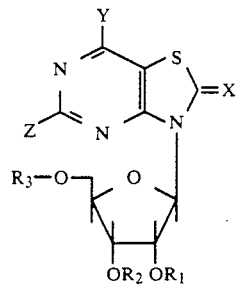

where $R_1$ and $R_2$ individually are H or $C_1$-$C_{18}$ acyl and $R_3$ is H, $C_1$-$C_{18}$ acyl or

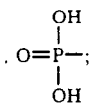

or $R_1$ is H and together $R_2$ and $R_3$ are

and X is $=$O or $=$S; Y is —OH, —SH, —NH$_2$ or halogen; and Z is H, —NH$_2$, —OH or halogen; wherein halogen is Cl or Br; or a pharmaceutically acceptable salt thereof.

3. A method of claim 1 wherein:
   Z is —NH$_2$ and Y is —OH.

4. A method of claim 3 wherein:
   $R_1$ and $R_2$ are H, acetyl or benzoyl and $R_3$ is H, acetyl, benzoyl or

or $R_1$ is H and together $R_2$ and $R_3$ are $$O=\overset{|}{\underset{OH}{P}}-;$$

or a pharmaceutically acceptable salt thereof.

5. A method of claim 4 wherein:
   Z is —NH$_2$ and Y is —OH.

6. A method of claim 5 wherein:
   X is $=$O.

7. A method of claim 4 wherein:
   $R_1$ and $R_2$ are H.

8. A method of claim 7 wherein:
   $R_3$ is H.

9. A method of enhancing an immune response of natural killer immune cells in a mammalian host consisting essentially of:
   administering to said host an effective amount of a pharmaceutical composition containing as the active component therein 5-amino-3-β-D-ribofuranosylthiazolo[4,5-d]pyrimidine-2,7(6H)- dione or a pharmaceutically acceptable salt thereof.

10. A method of enhancing an immune response of macrophage cells in a mammalian host consisting essentially of:
administering to said host an effective amount of a pharmaceutical composition containing as the active component therein 5-amino-3-β-D-ribofuranosylthiazolo[4,5-d]pyrimidine-2,7(6H)-dione or a pharmaceutically acceptable salt thereof.

11. A method of enhancing an immune response of lymphocyte cells in a mammalian host consisting essentially of:
administering to said host an effective amount of a pharmaceutical composition containing as the active component therein 5-amino-3-β-D-ribofuranosylthiazolo[4,5-d]pyrimidine-2,7(6H)-dione or a pharmaceutically acceptable salt thereof.

12. A compound of the structure:

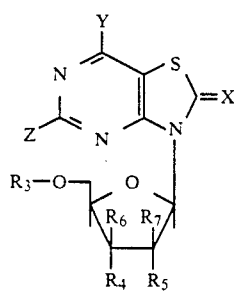

wherein $R_4$, $R_5$, $R_6$ and $R_7$ individually are H, OH or $C_1-C_{18}$ O-acyl and $R_3$ is H, $C_1-C_{18}$ acyl or

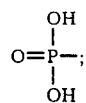

or $R_5$ and $R_7$ are H or OH, $R_6$ is H and together $R_3$ and $R_4$ are

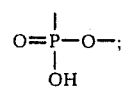

and X is =O or =S; Y is —OH, —SH, —NH$_2$ or halogen; and Z is H, —NH$_2$, —OH or halogen; wherein halogen is Cl or Br; or a pharmaceutically acceptable salt thereof.

13. A compound of claim 28 wherein:
said compound is of the structure:

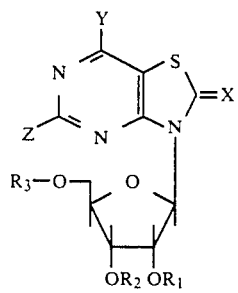

wherein $R_1$ and $R_2$ individually are H or $C_1-C_{18}$ acyl and $R_3$ is H, $C_1-C_{18}$ acyl or

or $R_1$ is H and together $R_2$ and $R_3$ are

and X is =O or =S; Y is —OH, —SH, —NH$_2$ or halogen; and Z is H, —NH$_2$, —OH or halogen; wherein halogen in Cl or Br; or a pharmaceutically acceptable salt thereof.

14. A compound of claim 12 wherein:
Z is —NH$_2$ and Y is —OH.

15. A compound of claim 13 wherein:
$R_1$ and $R_2$ are H, acetyl or benzoyl and $R_3$ is H, acetyl, benzoyl or

or $R_1$ is H and together $R_2$ and $R_3$ are

or a pharmaceutically acceptable salt thereof.

16. A compound of claim 15 wherein:
Z is —NH$_2$ and Y is —OH.

17. A compound of claim 16 wherein:
X is =O.

18. A compound of claim 15 wherein:
$R_1$ and $R_2$ are H.

19. A compound of claim 18 wherein:
$R_3$ is H.

20. 5-amino-3-β-D-ribofuranosylthiazolo[4,5-d]pyrimidine-2,7(6H)-dione or a pharmaceutically acceptable salt thereof.

21. The 5'-phosphate of the compound of claim 20.

22. The 3'-5' cyclic phosphate of the compound of claim 20.

23. 5-amino-2-thioxo-3-β-D-ribofuranosylthiazolo[4,5-d]-pyrimidin-7(6H)-one.

* * * * *

UNITED STATES PATENT AND TRADEMARK OFFICE
CERTIFICATE OF CORRECTION

PATENT NO. : 5,041,426
DATED : August 20, 1991
INVENTOR(S) : Roland K. Robins, et. al.

It is certified that error appears in the above-indentified patent and that said Letters Patent is hereby corrected as shown below:

On the Title page, item [57], on the fourth and fifth to last line of the Abstract, "$Nh_2$" should read --$NH_2$--.

Column 21 and 22, under "continued Scheme III" and "Scheme V" Structures 19, 20, 27, 28, 29 and 30 should read as shown on attached sheets--.

Column 21, structures 27 and 29 of scheme 5 have been over printed on structure 19 of scheme 3--.

Column 47, line 1, claim 13, the numeral "28" should read --12--.

Signed and Sealed this

Seventeenth Day of August, 1993

Attest:

BRUCE LEHMAN

*Attesting Officer*   *Commissioner of Patents and Trademarks*

-continued
SCHEME III
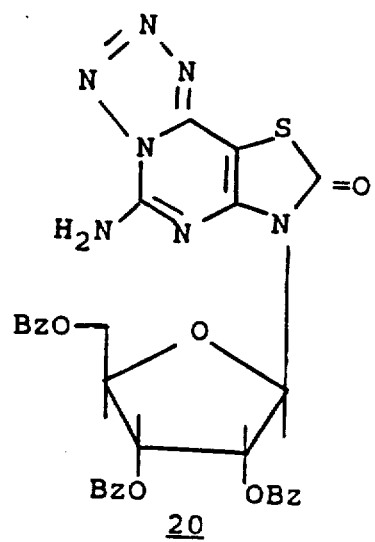 20
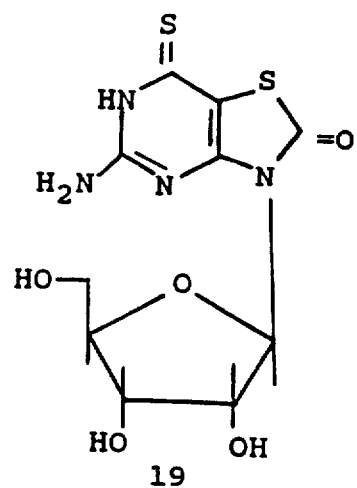 19